(12) United States Patent
Wall

(10) Patent No.: US 11,559,338 B1
(45) Date of Patent: Jan. 24, 2023

(54) SPINAL IMPLANT SYSTEM AND METHOD

(71) Applicant: WARSAW ORTHOPEDIC INC., Warsaw, IN (US)

(72) Inventor: Daniel Paxton Wall, Cordova, TX (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/527,459

(22) Filed: Nov. 16, 2021

(51) Int. Cl.
*A61B 17/70* (2006.01)

(52) U.S. Cl.
CPC ........ *A61B 17/7082* (2013.01); *A61B 17/702* (2013.01); *A61B 17/7032* (2013.01); *A61B 17/708* (2013.01); *A61B 17/7076* (2013.01)

(58) Field of Classification Search
CPC ............ A61B 17/7082; A61B 17/7076; A61B 17/7077; A61B 17/7079; A61B 17/708; A61B 17/7074; A61B 17/7083; A61B 17/7086; A61B 17/7091
See application file for complete search history.

(56) References Cited

U.S. PATENT DOCUMENTS

| | | | | |
|---|---|---|---|---|
| 6,299,616 | B1* | 10/2001 | Beger | A61B 17/7044 606/86 R |
| 8,784,431 | B1* | 7/2014 | Harder | A61B 17/7082 606/86 A |
| 10,448,978 | B2 | 10/2019 | Wall et al. | |
| 2008/0045970 | A1* | 2/2008 | Saidha | A61B 17/7035 81/436 |
| 2010/0160982 | A1* | 6/2010 | Justis | A61B 17/7089 606/86 A |
| 2014/0324062 | A1* | 10/2014 | Heuer | A61B 17/7082 606/104 |
| 2015/0250521 | A1* | 9/2015 | Poker | A61B 17/8875 606/104 |
| 2015/0282855 | A1* | 10/2015 | Bess | A61B 17/7082 606/86 A |
| 2015/0359572 | A1* | 12/2015 | Reimels | A61B 17/7082 606/104 |
| 2018/0303522 | A1* | 10/2018 | Wall | A61B 34/20 |
| 2019/0029736 | A1 | 1/2019 | Wall et al. | |
| 2019/0029737 | A1* | 1/2019 | Wall | A61B 17/86 |
| 2020/0390478 | A1* | 12/2020 | Rodriguez | A61B 17/7001 |

* cited by examiner

*Primary Examiner* — Jan Christopher L Merene
*Assistant Examiner* — Anna V. Little
(74) *Attorney, Agent, or Firm* — Sorell, Lenna & Schmidt, LLP

(57) ABSTRACT

An instrument includes an outer sleeve defining a passageway and extending along an axis between proximal and distal ends. A knob sleeve is positioned in the passageway and defines a bore and a sleeve cavity. A latch is positioned in the sleeve cavity. A shaft is positioned in the bore. An inner sleeve is positioned between the knob sleeve and the shaft. A proximal end of the inner sleeve defines a notch. The knob sleeve is movable relative to the outer sleeve to move the instrument between a first orientation in which the latch is positioned in the notch and the inner sleeve is prevented from translating along the axis and a second orientation in which the latch is spaced apart from the notch and the inner sleeve is translatable along the axis. Systems, implants and methods are disclosed.

20 Claims, 27 Drawing Sheets

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone screws can be delivered to a surgical site. The rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument comprises an outer sleeve extending along a longitudinal axis between opposite proximal and distal ends. The outer sleeve defines a passageway. A knob sleeve is positioned in the passageway. The knob sleeve defines a bore and a sleeve cavity. A latch is positioned in the sleeve cavity. A shaft is positioned in the bore and comprises a proximal end extending through the proximal end of the outer sleeve and a distal end extending through the distal end of the outer sleeve. The distal end of the shaft comprises a drive. An inner sleeve has a proximal end positioned between the knob sleeve and the shaft and an opposite distal end comprising a threaded outer surface. The proximal end of the inner sleeve defines a notch. The knob sleeve is movable relative to the outer sleeve to move the instrument between a first orientation in which the latch is positioned in the notch and the inner sleeve is prevented from translating relative to the outer sleeve along the longitudinal axis and a second orientation in which the latch is spaced apart from the notch and the inner sleeve is translatable relative to the outer sleeve along the longitudinal axis. In some embodiments, systems, spinal implants and methods are disclosed.

In one embodiment, a surgical instrument includes an outer sleeve extending along a longitudinal axis between opposite proximal and distal ends. The proximal end defines an aperture. The distal end defines a passageway. A knob sleeve defines a bore and has a proximal portion positioned in the aperture and a distal portion positioned in the passageway. The proximal portion defines a first sleeve cavity and a second sleeve cavity. A knob is coupled to the proximal portion by spaced apart pins that each extend through the knob and into the knob shaft such that rotation of the knob relative to the outer sleeve also rotates the knob sleeve relative to the outer surface. The knob defines a first knob cavity aligned with the first sleeve cavity and a second knob cavity aligned with the second sleeve cavity. A first latch has a first end positioned in the first knob cavity and a second end positioned in the first sleeve cavity. The first latch has a spring positioned in a hole in the first end of the first latch. A second latch has a first end positioned in the second knob cavity and a second end positioned in the second sleeve cavity. The second latch has a spring positioned in a hole in the first end of the second latch. A shaft is positioned in the bore and comprises a proximal end extending through the proximal end of the outer sleeve and a distal end extending through the distal end of the outer sleeve. The distal end of the shaft comprises a drive. The shaft is permanently fixed relative to the outer sleeve. An inner sleeve has a proximal end positioned between the knob sleeve and the shaft and an opposite distal end comprising a threaded outer surface. The proximal end of the inner sleeve includes a circumferential notch. The knob is movable relative to the outer sleeve to move the instrument between a first orientation in which the latches are positioned in the notch and the inner sleeve is prevented from translating relative to the outer sleeve along the longitudinal axis and a second orientation in which the latches are spaced apart from the notch and the inner sleeve is translatable relative to the outer sleeve along the longitudinal axis.

In one embodiment, a surgical instrument includes an outer sleeve extending along a longitudinal axis between opposite proximal and distal ends. The proximal end defines an aperture. The distal end defines a passageway. A knob sleeve defines a bore and has a proximal portion positioned in the aperture and a distal portion positioned in the passageway. The proximal portion defines a first sleeve cavity and a second sleeve cavity. A knob is coupled to the proximal portion by spaced apart pins that each extend through the knob and into the knob shaft such that rotation of the knob relative to the outer sleeve also rotates the knob sleeve relative to the outer surface. The knob defines a first knob cavity aligned with the first sleeve cavity and a second knob cavity aligned with the second sleeve cavity. A first latch has a first end positioned in the first knob cavity and a second end positioned in the first sleeve cavity. The first latch has a spring positioned in a hole in the first end of the first latch. The second end of the first latch includes a first ramp. A second latch has a first end positioned in the second knob cavity and a second end positioned in the second sleeve cavity. The second latch has a spring positioned in a hole in the first end of the second latch. The second end of the second latch includes a second ramp. A shaft is positioned in the bore and comprises a proximal end extending through the proximal end of the outer sleeve and a distal end extending through the distal end of the outer sleeve. The distal end of the shaft comprises a drive. The shaft is permanently fixed relative to the outer sleeve. An inner sleeve has a proximal end positioned between the knob sleeve and the shaft and an opposite distal end comprising a threaded outer surface. The proximal end of the inner sleeve includes a circumferential flange defining a circumferential ramp and a notch. The knob is movable relative to the outer sleeve to move the instrument between a first orientation, a second orientation and a third orientation. The inner sleeve is distal to the bore when the instrument is in the first orientation. The latches are positioned in the notch when the instrument is in the second orientation such that the inner sleeve is prevented from translating relative to the outer sleeve along the longitudinal axis. The latches are spaced apart from the notch and a portion of the inner sleeve is positioned in the bore when the instrument is in the third orientation such that the inner sleeve is translatable relative to the outer sleeve along the longitudinal axis. The circumferential ramp slides along the ramps of the latches as the instrument moves from the first orientation to the second orientation.

BRIEF DESCRIPTION OF THE DRAWINGS

The present disclosure will become more readily apparent from the specific description accompanied by the following drawings, in which.

Like reference numerals indicate the same or similar parts throughout the figures.

DETAILED DESCRIPTION

Figure 1:
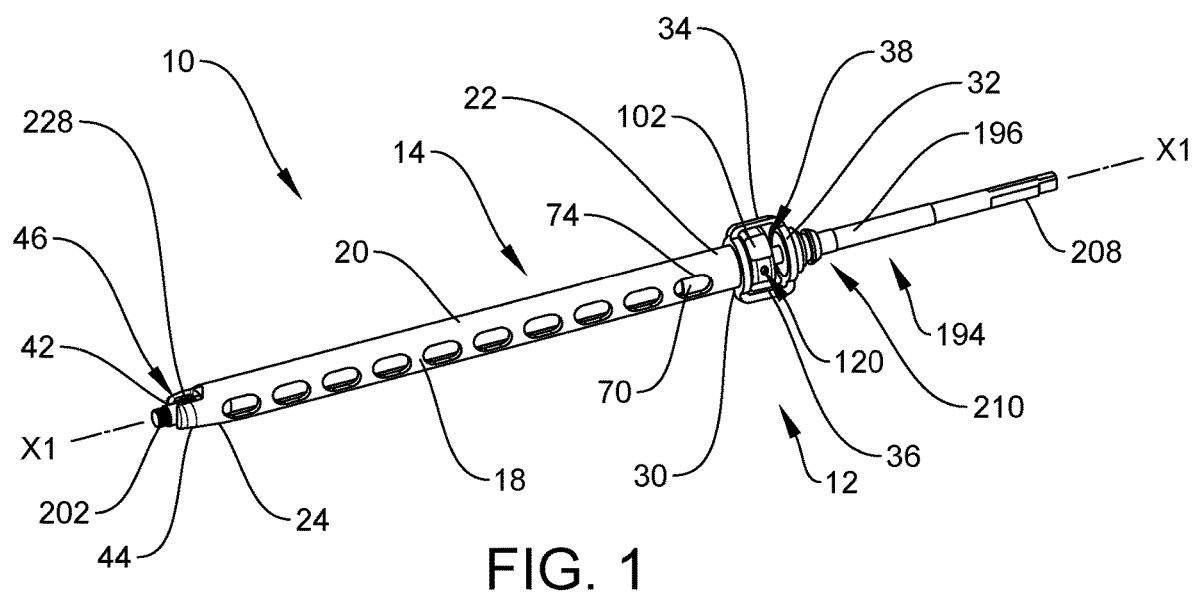
FIG. 1 is a perspective view of components of one embodiment of a surgical instrument of a surgical system, in accordance with the principles of the present disclosure.
Figure 2:
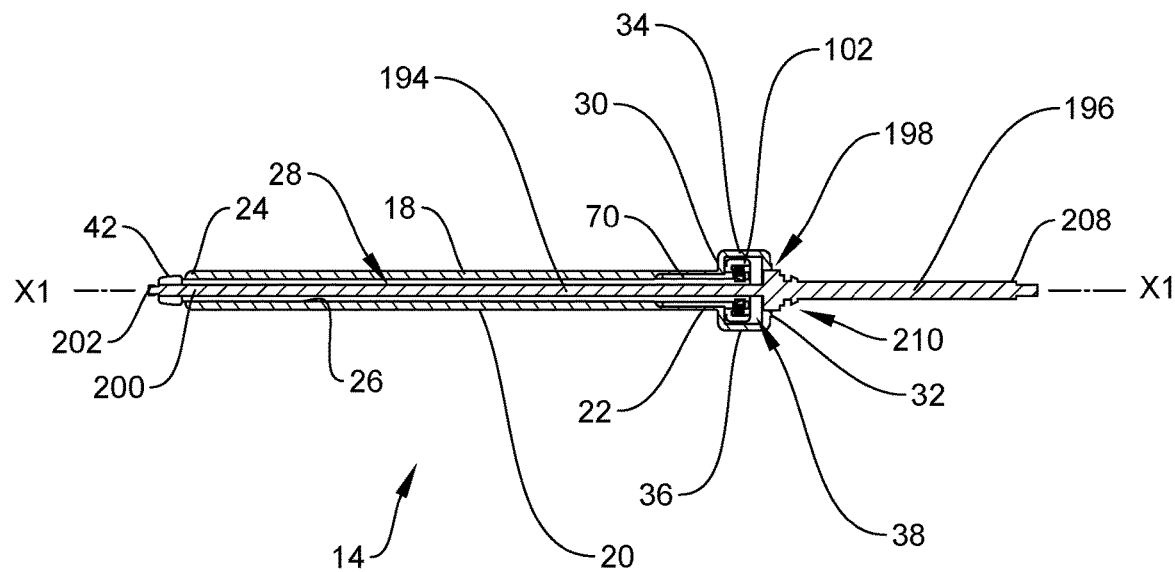
FIG. 2 is a side, cross-sectional view of the surgical instrument shown in FIG. 1.
Figure 3:
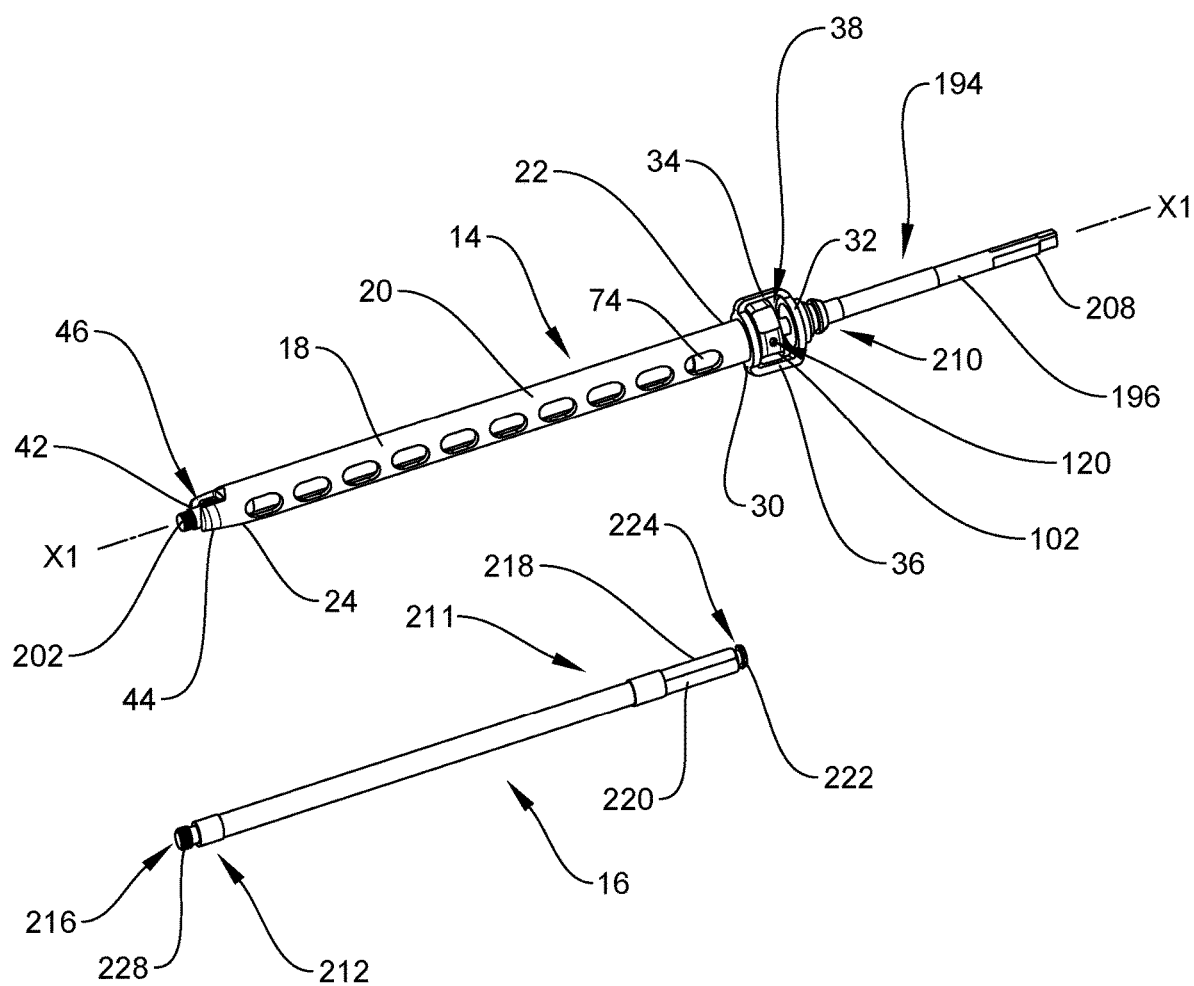
FIG. 3 is a perspective view of components of the surgical instrument shown in FIG. 1.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system comprises a surgical instrument that comprises a screw driver that can be employed with bone screws. In some embodiments, the present surgical system includes a surgical instrument that can easily connect and disconnect from a bone screw. In some embodiments, the present surgical system includes a surgical instrument that can be employed with an end effector of a robotic arm to facilitate implant with the robotic arm. In some embodiments, the surgical instrument is guided through the end effector for a guide-wireless screw insertion. In some embodiments, the surgical instrument comprises a robot screw driver employed with robotic and/or navigation guidance, which may include an image guide.

In some embodiments, the present surgical system includes a screw driver configured for use with a robot, such as, for example, a Mazor robot to deliver screws during a surgical procedure, such as, for example, minimally invasive transforaminal lumbar interbody fusion (TLIF). The screw driver includes an inner sleeve that is connected to the screw such that instruments, for example, can be delivered through the inner sleeve to the head of the screw. In particular, the screw driver includes a disengagement feature in a knob of the screw driver that allows the inner sleeve of the screw driver to be left in the head of the screw when an outer sleeve assembly of the screw driver is removed. This allows a surgeon to disengage and/or remove the outer sleeve yet still guide other instruments down to the head of the screw via the inner sleeve.

In some embodiments, the screw driver is configured for use with different types of screws, such as, for example, screws having different sizes and/or structural configurations. In some embodiments, the screw driver is assembled by inserting the inner sleeve into an outer sleeve assembly that includes, among other things, the outer sleeve. In some embodiments, a hex of the inner sleeve is aligned with a hex of a knob sleeve of the outer sleeve assembly by pushing the inner sleeve from the distal end and pushing on a knob of the outer sleeve assembly that is coupled to the knob sleeve from the proximal end. In some embodiments, the inner sleeve is configured to snap into the outer sleeve assembly.

To remove the outer sleeve assembly from the screw after driving the screw into tissue, such as, for example, bone, the surgeon pulls up on the knob (proximal direction) while pulling back on the outer sleeve. The outer sleeve assembly can then be removed from the screw while leaving the inner sleeve threaded into the head of the screw. In some embodiments, pulling up on the knob (proximal direction) while pulling back on the outer sleeve causes snap latches in the knob and knob sleeve to disengage, allowing the outer sleeve assembly to slide off of the inner sleeve. In some embodiments, pins on the latches ride up ramps in the knob, pulling them outwards and disengaging the latch.

In some embodiments, the outer sleeve assembly includes a drive shaft that is one piece with the outer sleeve. In some embodiments, the drive shaft is welded to the outer sleeve. In some embodiments, the knob and the knob sleeve are keyed together and turn together. In some embodiments, spring loaded ramps in the knob and knob sleeve snap back on insertion of the inner sleeve and then retain it once loaded. In some embodiments, the knob is spring biased relative to the knob sleeve by four springs (about 5 lbsf axial). In some embodiments, pins key and retain the knob after assembly.

In some embodiments, the outer sleeve assembly is constructed by sliding the knob into a window in the outer sleeve. Four springs are then loaded into the knob sleeve and the knob sleeve is inserted into the knob. Snap latches and springs are inserted from inside the window in the outer sleeve. The knob sleeve is then fully seated and retained by inserting two pins and laser welding. The driver shaft is inserted and welded to complete construction of the outer sleeve assembly.

In some embodiments, the driver shaft includes a drive, such as, for example, a drive tip that engages a bone screw. In some embodiments, the outer shaft and the driver shaft are of one piece construction. In some embodiments, the one piece construction allows tolerances to be controlled tightly for improved accuracy of trajectory during implant insertion. In some embodiments, the drive tip includes a Torx configuration. In some embodiments, the inner sleeve includes a male thread configured to mate with one or more female threads of a receiver of a bone screw to resist and/or prevent disengagement of the inner sleeve from the receiver.

In some embodiments, the screw driver is configured for use with robotic surgery. In some embodiments, the screw driver can be employed with fixed-axis screws (FAS), uni-axial screws (UAS), sagittal adjusting screws (SAS), transverse sagittal adjusting screws (TSAS) and multi-axial screws (MAS) screws, and allows the screws to be driven through a robotic end effector In some embodiments, a method of assembling components of the present system includes the step of connecting a bone screw to the screw driver. In some embodiments, the method includes the step of inserting the drive tip of the driver shaft into a drive socket of the bone screw while aligning tab extenders of the outer sleeve in mating grooves of the bone screw. In some embodiments, the method includes the step of rotating the knob of the screw driver to tighten and pull the bone screw tight against the screw driver.

In some embodiments, the surgical system is employed with a method for treating spinal trauma and/or deformity disorders. In some embodiments, the surgical system is employed with a method for treating spinal trauma and/or deformity disorders with a minimally invasive surgical technique.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-40, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, such as, for example, a bone screw, at a surgical site of a patient, which includes, for example, a spine. In some embodiments, the spinal implant can include one or more components of one or more spinal constructs, such as, for example, interbody devices, interbody cages, bone screws, spinal rods, tethers, connectors, plates and/or bone graft, and can be employed with various surgical procedures including surgical treatment of a cervical, thoracic, lumbar and/or sacral region of a spine.

Spinal implant system 10 includes a surgical instrument, such as, for example, a driver 12. Driver 12 includes an outer sleeve assembly 14 and an inner sleeve 16 configured for removable engagement with assembly 14. Assembly 14 includes an outer sleeve 18. Sleeve 18 includes a body 20 extending along a central longitudinal axis X1 between a proximal end 22 and an opposite distal end 24. Body 20 includes an inner surface 26 defining a passageway 28. Sleeve 18 includes a plate 30 coupled to end 22 and a plate 32 that is connected to plate 30 by bifurcated arms 34, 36. Plates 30, 32 and arms 34, 36 define an aperture 38. Aperture 38 is in communication with passageway 28 via an opening 40 that extends through plate 30. In some embodiments, passageway 28, aperture 38 and/or opening 40 extend parallel to axis X1. In some embodiments, passageway 28, aperture 38 and/or opening 40 are coaxial with axis X1. In some embodiments, passageway 28, aperture 38 and/or opening 40 may be disposed at alternate orientations, relative to X1, such as, for example, transverse, perpendicular and/or other angular orientations such as acute or obtuse, co-axial and/or may be offset or staggered. In some embodiments, passageway 28, aperture 38 and/or opening 40 may have various cross section configurations, such as, for example, circular, oval, oblong, triangular, rectangular, square, polygonal, irregular, uniform, non-uniform, variable, tubular and/or tapered. In some embodiments, driver 12 is configured to be employed with an end effector of a robotic arm wherein driver 12 is guided through the end effector for guide-wireless insertion of a spinal implant, such as, for example, a bone screw, as discussed in U.S. patent application Ser. No. 15/492,867, U.S. patent application Ser. No. 15/661,962 and/or U.S. patent application Ser. No. 15/661,986, the contents of which is incorporated herein by reference, in their entireties.

Figure 4:
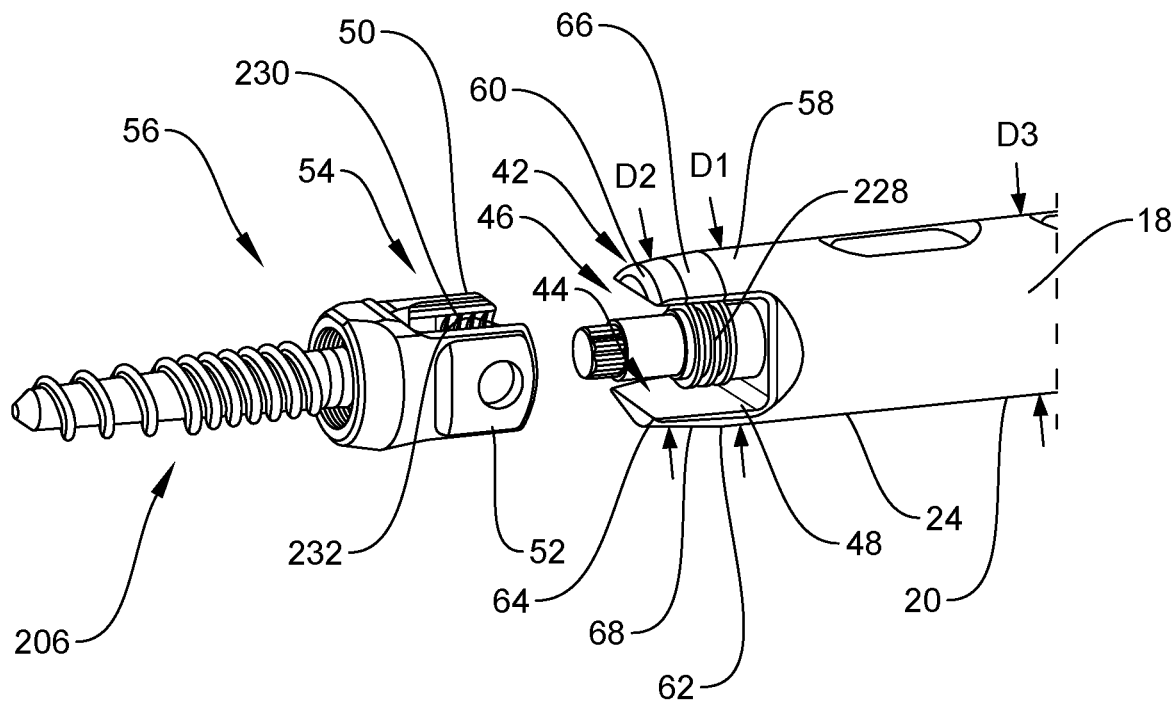
FIG. 4 is a perspective view of an implant of the system, in accordance with the principles of the present disclosure, and a portion of the surgical instrument shown in FIG. 1.
Figure 5:
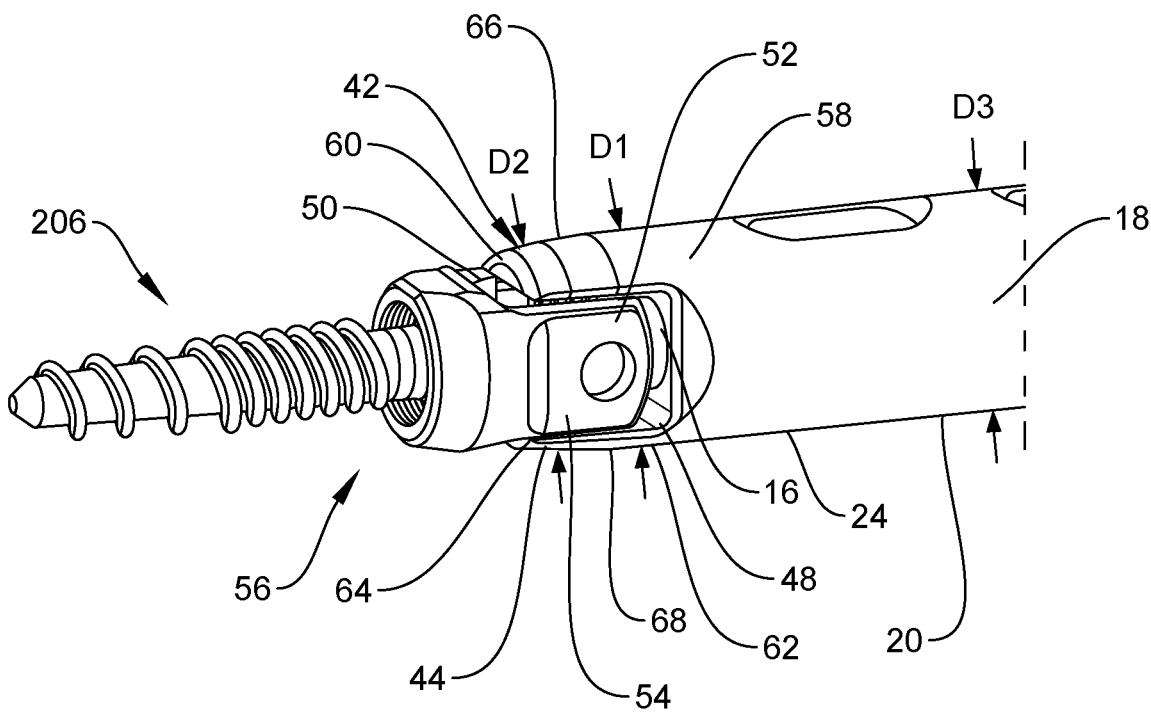
FIG. 5 is a perspective view of the implant shown in FIG. 4 coupled to a portion of the surgical instrument shown in FIG. 1.
Figure 6:
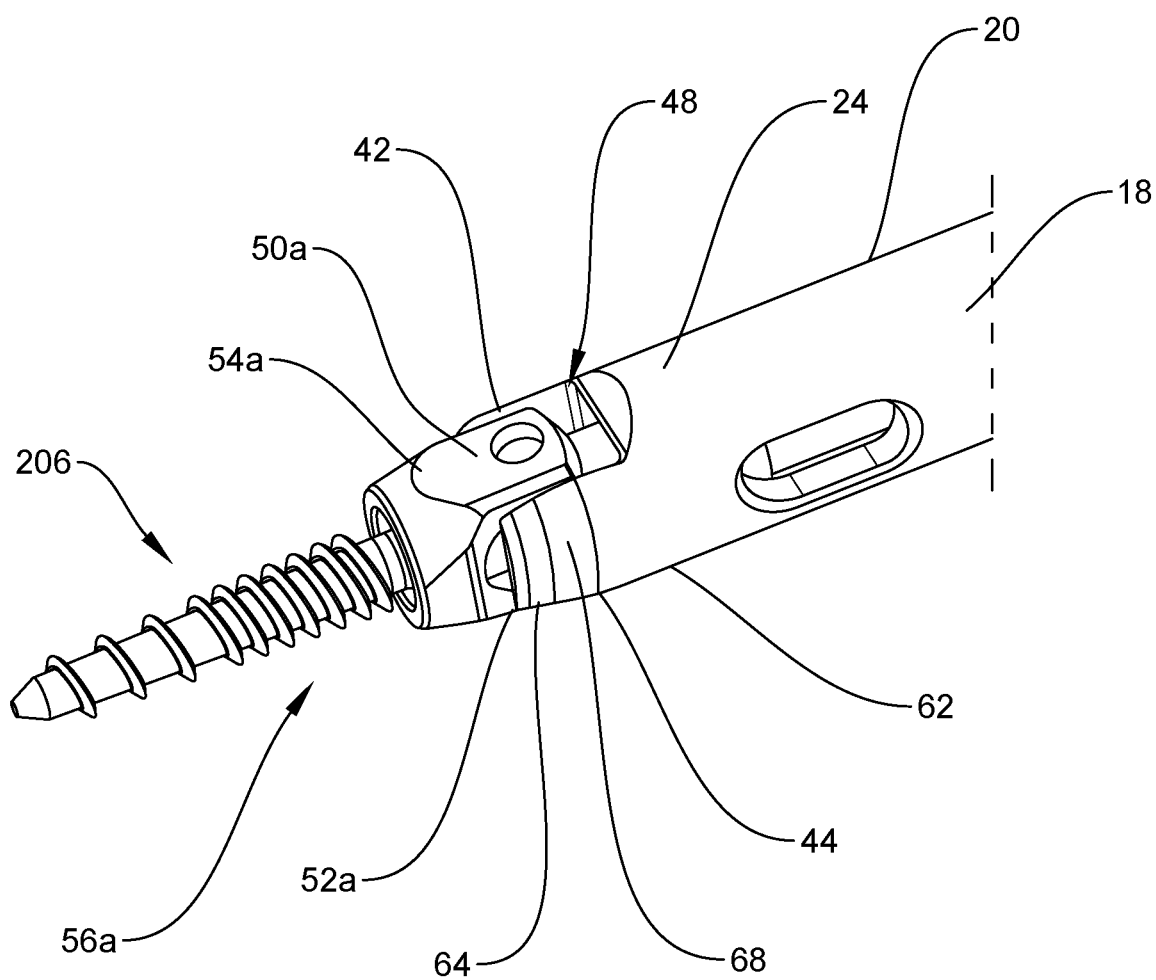
FIG. 6 is a perspective view of an implant of the system, in accordance with the principles of the present disclosure, coupled to a portion of the surgical instrument shown in FIG. 1.

In some embodiments, sleeve 18 includes spaced apart tabs 42, 44 coupled to end 24 such that tab 44 faces tab 42 and tabs 42, 44 define spaced apart recesses 46, 48 positioned therebetween. In some embodiment, tabs 42, 44 are integrally and/or monolithically formed with body 20. Tabs 42, 44 are spaced equidistantly apart about end 24 such that the width of recess 46 defined by a distance between tabs 42, 44 is equal to the width of recess 48 defined by a distance between tabs 42, 44. Tabs 42, 44 are configured for disposal between arms 50, 52 of a receiver 54 of an implant, such as, for example, a bone screw 56, as shown in FIGS. 4 and 5, for example. Arm 50 is positioned in recess 46 when tabs 42, 44 are positioned between arms 50, 52 and arm 52 is positioned in recess 48 when tabs 42, 44 are positioned between arms 50, 52. In some embodiments, tabs 42, 44 are configured for disposal between arms 50a, 52a of a receiver 54a of an implant, such as, for example, a bone screw 56a, as shown in FIG. 6, wherein receiver 54a is different in size than receiver 54.

Tab 42 includes a proximal end 58 coupled to end 24 and an opposite distal end 60 and tab 44 includes a proximal end 62 coupled to end 24 and an opposite distal end 64, as shown in FIGS. 4 and 5, for example. In some embodiments, an outer surface 66 of tab 42 is tapered along axis X1 from end 58 to end 60 and an outer surface 68 of tab 44 is tapered along axis X1 from end 62 to end 64. Due to the tapering of tabs 42, a distance D1 between surface 66 and surface 68 at ends 58, 62 is greater than a distance D2 between surface 66 and surface 68 at ends 60, 64. Ends 60, 64 define a distal tip of driver 12 that is tapered due to outer surfaces 66, 68 to ease insertion into a robotic arm guide and the patient. In some embodiments, an outer diameter D3 of body 20 is equal to distance D1. In some embodiments, diameter D3 is the maximum diameter of body 20 and distance D1 is the maximum distance between surface 66 and surface 68.

Assembly 14 includes a knob sleeve 70 extending through opening 40 and having a proximal portion 72 rotatably positioned in aperture 38 and a distal portion 74 rotatably positioned in passageway 28. An inner surface 76 of sleeve 70 defines a bore 78 configured for disposal of sleeve 16, as discussed herein. In some embodiments, surface 76 is shaped and/or configured to provide bore 78 with a hexagonal configuration for disposal of a portion of sleeve 16 having a hexagonal configuration such that rotating sleeve 70 relative to sleeve 18 also rotates sleeve 16 relative to sleeve 18, as discussed herein. Portion 72 includes a distal end surface 80 that directly engages a proximal surface 82 of plate 30 to maintain portion 72 in aperture 38 and prevent portion 72 from moving distally into passageway 28. Indeed, portion 72 has a maximum diameter that is greater than a maximum diameter of opening 40 to prevent portion 72 from moving through opening 40.

In some embodiments, surface 80 and/or surface 82 extend perpendicular to axis X1 when portion 72 is positioned in aperture 38 and portion 74 is positioned in passageway 28. In some embodiments, bore 78 and/or the portion of sleeve 16 configured for disposal in bore may have various cross section configurations, such as, for example, circular, oval, oblong, triangular, rectangular, square, polygonal, irregular, uniform, non-uniform, variable, tubular and/or tapered.

Figure 7:
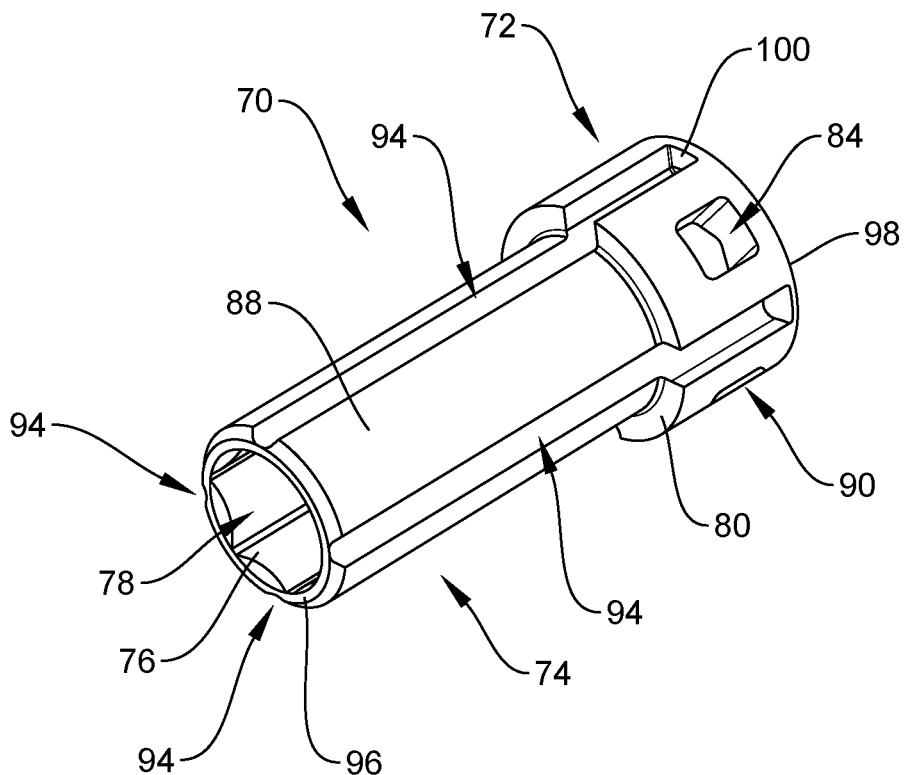
FIG. 7 is a perspective view of a component of the surgical instrument shown in FIG. 1.
Figure 8:
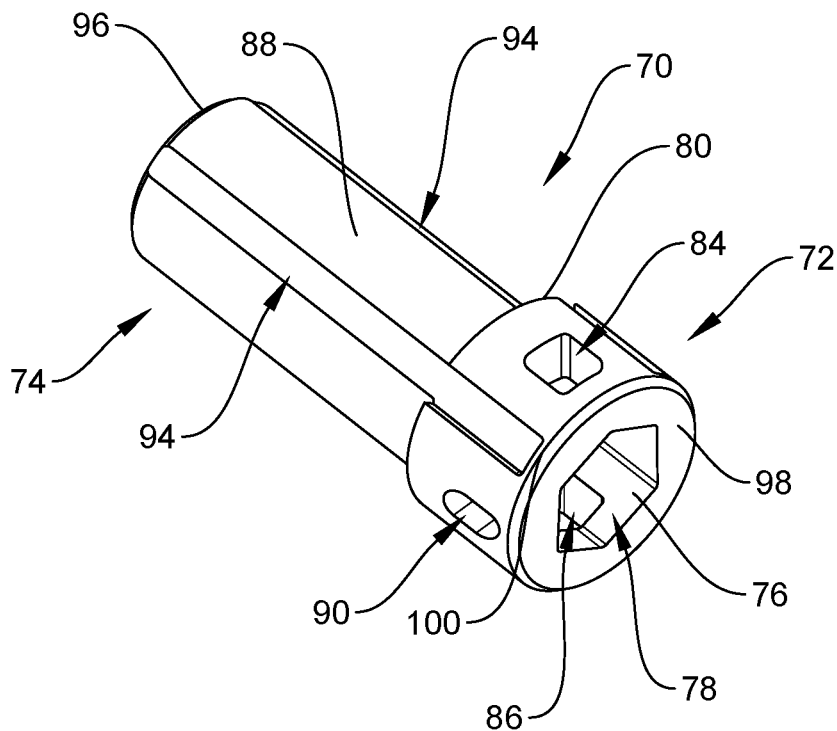
FIG. 8 is a perspective view of the component shown in FIG. 7.

Portion 72 defines a first sleeve cavity 84 and a second sleeve cavity 86, as shown in FIGS. 7 and 8, for example. Cavities 84, 86 are configured for disposal of spring-loaded latches, as discussed herein. Cavity 84 is spaced apart from cavity 86 such that cavity 86 is aligned with cavity 84. That is, cavity 86 is coaxial with cavity along a transverse axis that extends perpendicular to axis X1. Cavities 84, 86 each extend through surface 76 and an opposite outer surface 88 of sleeve 70 such that cavities 84, 86 are each in communication with bore 78. In some embodiments, cavities 84, 86 each have a square or rounded square shape, such as, for example, a squircle. In some embodiments, cavities 84, 86 each extend perpendicular to axis X1 when portion 72 is positioned in aperture 38 and portion 74 is positioned in passageway 28. In some embodiments, cavities 84, 86 may be variously shaped, such as, for example, oval, oblong, triangular, square, polygonal, irregular, uniform, non-uniform, offset, staggered, undulating, arcuate, variable and/or tapered. In some embodiments, cavities 84, 86 each have a configuration (e.g., size and/or shape) that complements that of latches that are disposed in cavities 84, 86, as discussed herein.

Portion 72 further defines a first slot 90 and a second slot 92. Slots 90, 92 are configured for disposal of pins to couple sleeve 70 to a knob, as discussed herein. Slot 90 is spaced apart from slot 92 such that slot 92 is aligned with slot 90. In some embodiments, slots 90, 92 are each positioned equidistant between cavities 84, 86. Slots 90, 92 each extend through surface 76 and surface 88 such that slots 90, 92 are each in communication with bore 78. In some embodiments, slots 90, 92 each have an oblong shape. In some embodiments, slots 90, 92 each extend perpendicular to axis X1 when portion 72 is positioned in aperture 38 and portion 74 is positioned in passageway 28.

Sleeve 70 defines a plurality of spaced apart grooves 94 extending into surface 88. In some embodiments, sleeve 70 includes four grooves 94, which are equally spaced apart from one another about sleeve 70. That is, grooves 94 are spaced radially about sleeve 70 such that grooves 94 are each spaced ninety degrees from an adjacent one of grooves 94. Grooves 94 are configured for disposal of springs to bias a knob, as discussed herein. In some embodiments, grooves 94 each extend parallel to axis X1 when portion 72 is positioned in aperture 38 and portion 74 is positioned in passageway 28. Grooves 94 each extend through a distal end surface 96 of portion 74 without extending through a proximal end surface 98 of portion 72 such that springs directly engage a wall 100 that defines surface 98 when the springs are positioned in grooves 94, as discussed herein.

Figure 9:
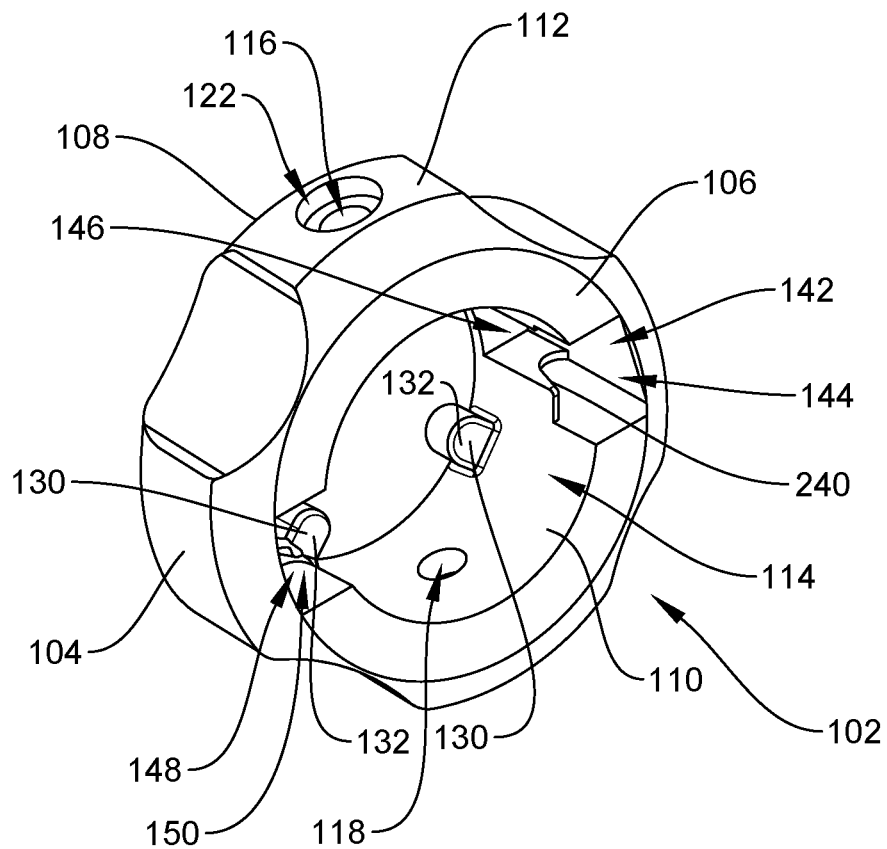
FIG. 9 is a perspective view of a component of the surgical instrument shown in FIG. 1.
Figure 10:
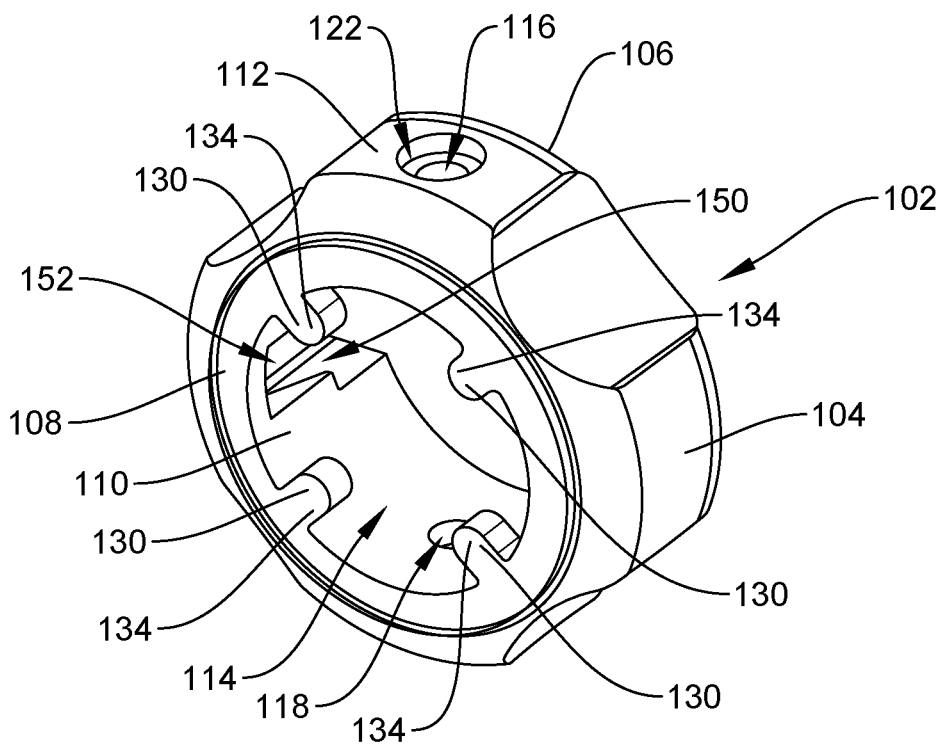
FIG. 10 is a perspective view of the component shown in FIG. 9.

Assembly 14 includes a knob 102 coupled to sleeve 70 such that knob 102 is rotatably positioned in aperture 38. Knob 102 includes a wall 104 including a proximal surface 106 and an opposite distal surface 108, as shown in FIGS. 9 and 10, for example. Wall 104 includes an inner surface 110 and an opposite outer surface 112. Surfaces 110, 112 extend from surface 106 to surface 108. Surface 110 defines a channel 114 extending through surface 106 and surface 108. Portion 72 of sleeve 70 is positioned in channel 114. Knob 102 includes a first pin hole 116 and a second pin hole 118 that is spaced apart from hole 116 such that hole 118 is aligned with hole 116. Holes 116, 118 each extend through surfaces 110, 112 such that holes 116, 118 are each in communication with channel 114. Hole 116 is aligned with slot 90 and hole 118 is aligned with slot 92 when knob 102 is coupled to sleeve 70. Assembly 14 includes a plurality of pins, such as, for example, pins 120 to couple knob 102 to sleeve 70. In particular, a first one of pins 120 extends through hole 116 and into slot 90 and a second one of pins 120 extends through hole 118 and into slot 92 to couple knob 102 to sleeve 70. Pins 120 are configured to translate within holes 116, 118 as knob 102 translates relative to sleeve 70, as discussed herein. The arrangement of pins 120 with knob 102 and sleeve 70 keys knob 102 and sleeve 70 together such that rotation of knob 102 relative to sleeve 18 about axis X1 also rotates sleeve 70 relative to sleeve 18 about axis X1 and/or rotation of sleeve 70 relative to sleeve 18 about axis X1 also rotates knob 102 relative to sleeve 18 about axis X1. Due to the alignment of slots 90, 92 and the alignment of holes 116, 118, the pin 120 in hole 116 and slot 90 is coaxial with the pin 120 in hole 118 and slot 92.

In some embodiments, knob 102 includes a first counterbore 122 in communication with hole 116 and a second counterbore 124 in communication with hole 118. This allows a head 126 of the pin 120 that is disposed in hole 116 and counterbore 122 to be disposed entirely within counterbore 122 while a shaft 128 of the pin 120 that is disposed in hole 116 and counterbore 122 to be disposed in hole 116 and head 126 of the pin 120 that is disposed in hole 118 and counterbore 124 to be disposed entirely within counterbore 124 while shaft 128 of the pin 120 that is disposed in hole 118 and counterbore 124 is disposed in hole 118. Disposing heads 126 entirely within counterbores 122, 124 prevents pins 120 from extending outwardly from surface 112 to facilitate gripping of knob 102 by hand.

Figures 11, 12:
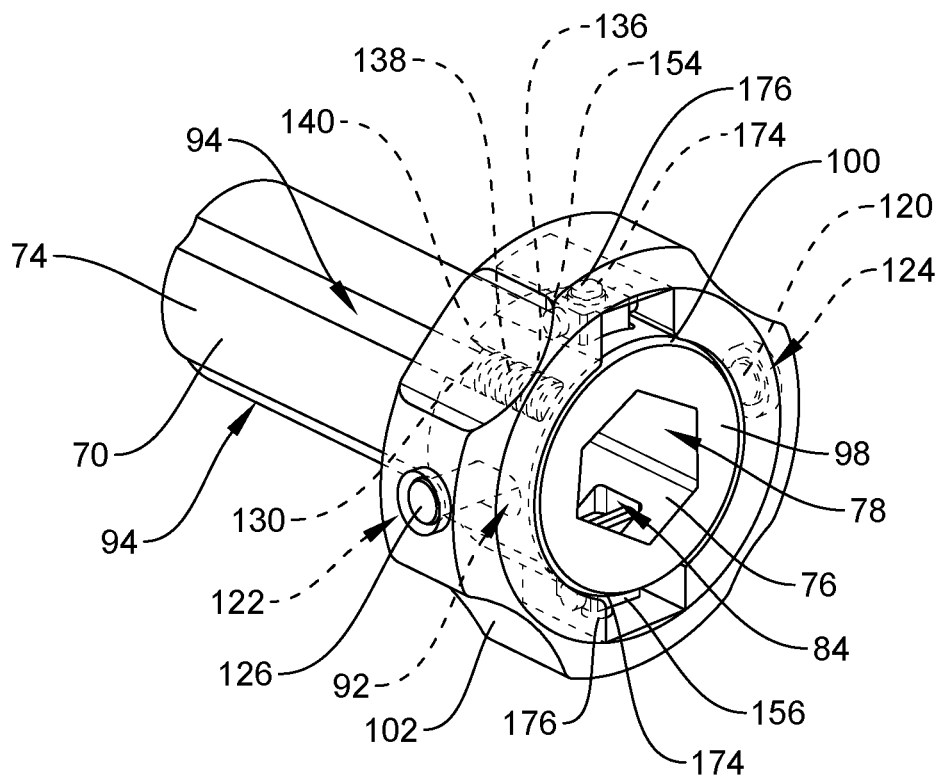
FIG. 11 is a perspective view of components of the surgical instrument shown in FIG. 1.
FIG. 12 is a perspective view of components of the surgical instrument shown in FIG. 1.
Figure 13:
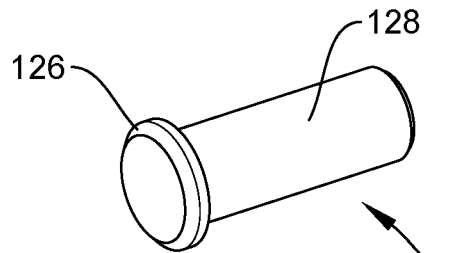
FIG. 13 is a perspective view of a component of the surgical instrument shown in FIG. 1.

Knob 102 includes a plurality of spaced apart tabs 130 extending outwardly from surface 110 such that tabs 130 are disposed radially about knob 102, as shown in FIGS. 9 and 10, for example. In some embodiments, knob 102 includes four tabs 130, wherein each tab 130 is aligned with one of grooves 94 when knob 102 is coupled to sleeve 70. Tabs 130 each include a proximal surface 132 and an opposite distal surface 134 that is flush with surface 108. The alignment of tabs 130 with grooves 94 allows proximal ends 136 of springs 138 to directly engage wall 100 and opposite distal ends 140 of springs 138 to directly engage one of surfaces 132 when springs 138 are disposed in grooves 94, as shown in FIGS. 11 and 12, for example. The arrangement of springs 138 with knob 102 and sleeve 70 biases knob 102 relative to sleeve 70 such that surface 108 of knob 102 directly engages surface 82 of plate 30, as discussed herein. That is, a force is required to overcome the force provided by springs 138 to allow knob 102 to be moved proximally along axis X1 relative to sleeve 18 such that surface 108 of knob 102 is spaced apart from surface 82 of plate 30. In some embodiments, springs 138 extend parallel to axis X1, when sleeve 70 is positioned in passageway 28 and knob 102 is coupled to sleeve 70.

Knob 102 includes a first knob cavity 142 having a proximal portion 144 extending through surface 106 and a distal portion 146 aligned with cavity 84. Knob 102 further includes a second knob cavity 148 that is spaced apart from cavity 142 and includes a proximal portion 150 extending through surface 106 and a distal portion 152 aligned with cavity 86. A first latch 154 includes a first end 156 positioned in portion 146 and a second end 158 positioned in cavity 84. A second latch 160 includes a first end 162 positioned in portion 152 and a second end 164 positioned in cavity 86.

Figure 14:
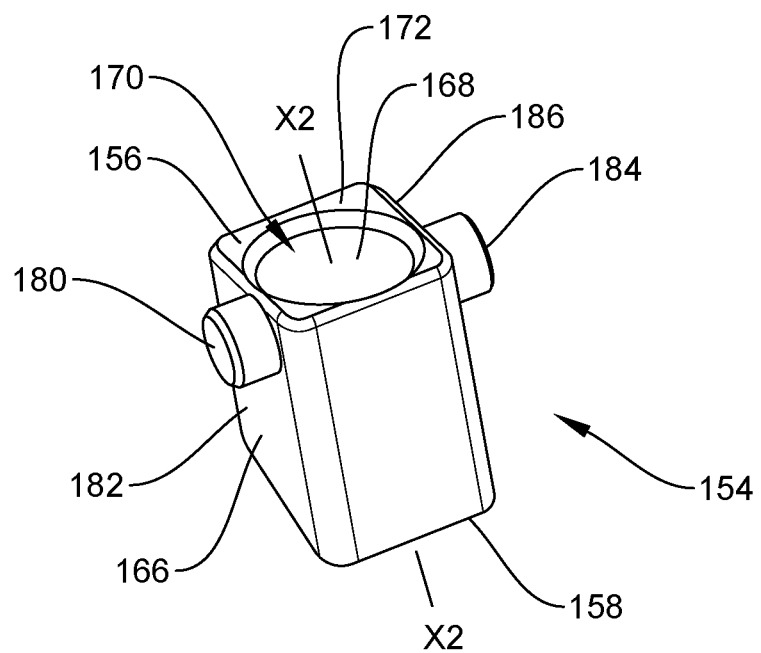
FIG. 14 is a perspective view of a component of the surgical instrument shown in FIG. 1.
Figure 15:
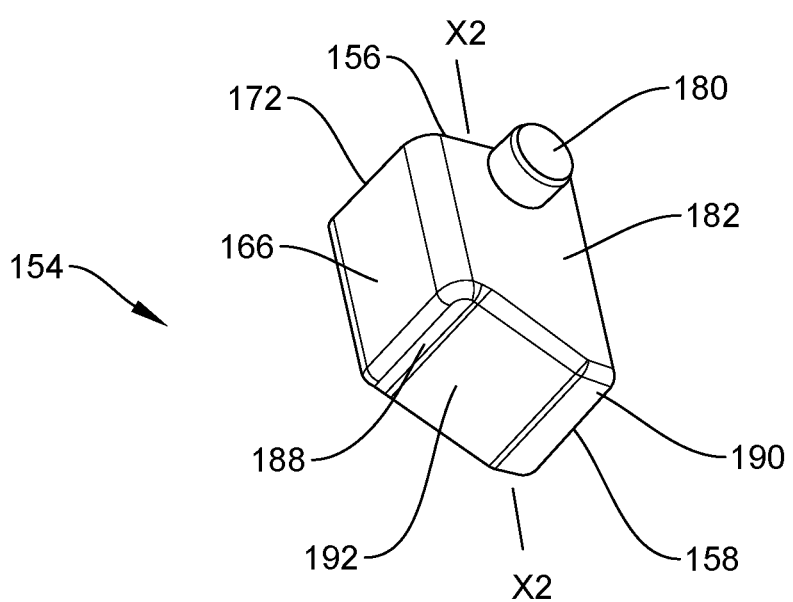
FIG. 15 is a perspective view of the component shown in FIG. 14.

Latches 154, 160 are identical and each include a body 166 defining ends 156, 158, as shown in FIGS. 14 and 15, for example. Body 166 extends along a central longitudinal axis X2 from end 156 to end 158. Body 166 includes an inner surface 168 defining a blind hole, such as, for example, a hole 170. Hole 170 is coaxial with axis X2 and extends through an end surface 172 of end 156. In some embodiments, surface 172 extends perpendicular to axis X2. Hole 170 is configured for disposal of a spring 174. In particular, spring 174 includes an end 176 positioned in portion 146 of cavity 142 or portion 152 of cavity 148 such that end 176 directly engages surface 110 of knob 102 and an opposite end 178 positioned in hole 170 such that end 178 directly engages a surface of body 166 extending perpendicular to axis X2. Springs 174 are configured to bias latches 154, 160 such that ends 158, 164 of latches 154, 160 are positioned in bore 78 of sleeve 70, as discussed herein. That is, a force is required to overcome the force provided by springs 174 to move ends 158, 164 of latches 154, 160 from a position in which ends 158, 164 of latches 154, 160 are positioned in bore 78 to a position in which ends 158, 164 of latches 154, 160 are spaced apart from bore 78. In some embodiments, springs 174 extend perpendicular to axis X1 when latches 154, 160 are assembled with knob 102, sleeve 70 and sleeve 18, as discussed herein.

Latches 154, 160 include a pin, such as, for example, a peg 180 extending from a side 182 of body 166 and a pin, such as, for example, a peg 184 extending from an opposite side 186 of body 166 such that peg 184 is aligned with peg 180. That is, peg 184 is coaxial with peg 186 along a transverse axis that extends perpendicular to axis X2. In some embodiments, pegs 180, 184 are cylindrical and are configured to ride along ramps 240 of knob 102 to disengage latches 154, 160 from sleeve 16, as discussed herein. In some embodiments, peg 180 and/or peg 184 may be variously configured and dimensioned, such as, for example, angled, concave, polygonal, irregular, uniform, non-uniform, staggered, tapered, consistent or variable, depending on the requirements of a particular application.

A distal end of body 166 includes a surface 188, a surface 190 and a ramp 192 extending continuously from surface 188 to surface 190. Surfaces 188, 190 each extend perpendicular to axis X2 and ramp 192 extends at a non-zero and/or acute angle relative to axis X1. Ramp 192 is configured to ride along a ramp of sleeve 16 as sleeve 16 is moved relative to sleeve 18 from an orientation in which sleeve 16 is able to translate relative to sleeve 18 along axis X1 to an orientation in which sleeve 16 is prevented from translating relative to sleeve along axis X1, as discussed herein. In some embodiments, ramp 192 may be disposed at alternate orientations, relative to axis X2, such as, for example, transverse and/or other angular orientations such as acute or obtuse, and/or may be offset or staggered.

Assembly 14 includes a shaft 194 that is coupled to sleeve 18 such that shaft 194 is coaxial with axis X1 and is permanently fixed relative to sleeve 18. That is, shaft 194 cannot be removed from sleeve 18 without breaking shaft 194 and/or sleeve 18. In some embodiments, shaft 194 is permanently fixed to sleeve 18 by welding shaft 194 to sleeve 18. Shaft 194 includes a proximal end 196 extending through an opening 198 in plate 32 and an opposite distal end 200 extending through bore 78 and passageway 28 such that a distal tip 202 of end 200 is distal to ends 60, 64 of tabs 42, 44. Tip 202 defines a bit, such as, for example, a drive that is configured for disposal in a correspondingly shaped socket 204 in a shaft 206 of bone screw 56 such that rotation of shaft 194 about axis X1 also rotates shaft 206 when tip 202 is disposed in socket 204. In some embodiments, tip 202 and socket each include a hexalobe geometry for a mating engagement therebetween. In some embodiments, tip 202 can alternatively include a cruciform, Phillips, square, hexagonal, polygonal, star cross sectional configuration for disposal in a correspondingly shaped socket 204.

End 196 includes a portion 208 configured to facilitate connection of driver 12 with a surgical instrument, such as, for example, an actuator/drill that is the same or similar to that disclosed in U.S. patent application Ser. No. 15/492,867, U.S. patent application Ser. No. 15/661,962 and/or U.S. patent application Ser. No. 15/661,986. In some embodiments, portion 208 includes quick connect surfaces or keyed geometry, such as, for example, triangle, hex, square or hexalobe to facilitate connection with the actuator/drill. End 196 further includes a portion 210 configured to facilitate connection of driver 12 with a navigation component, such as, for example, a navigation component that is the same or similar to that disclosed in U.S. patent application Ser. No. 15/492,867, U.S. patent application Ser. No. 15/661,962 and/or U.S. patent application Ser. No. 15/661,986 and is configured for operation with a navigation system that is the same or similar to that disclosed in U.S. patent application Ser. No. 15/492,867, U.S. patent application Ser. No. 15/661,962 and/or U.S. patent application Ser. No. 15/661,986.

Figure 16:
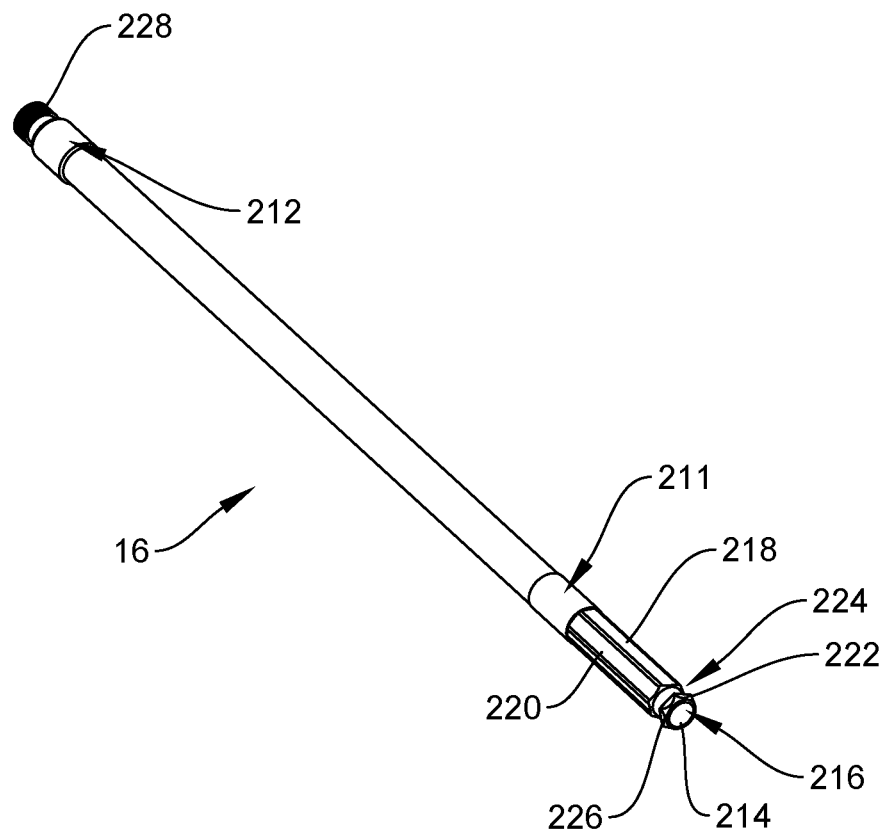
FIG. 16 is a perspective view of a component of the surgical instrument shown in FIG. 1.
Figure 17:
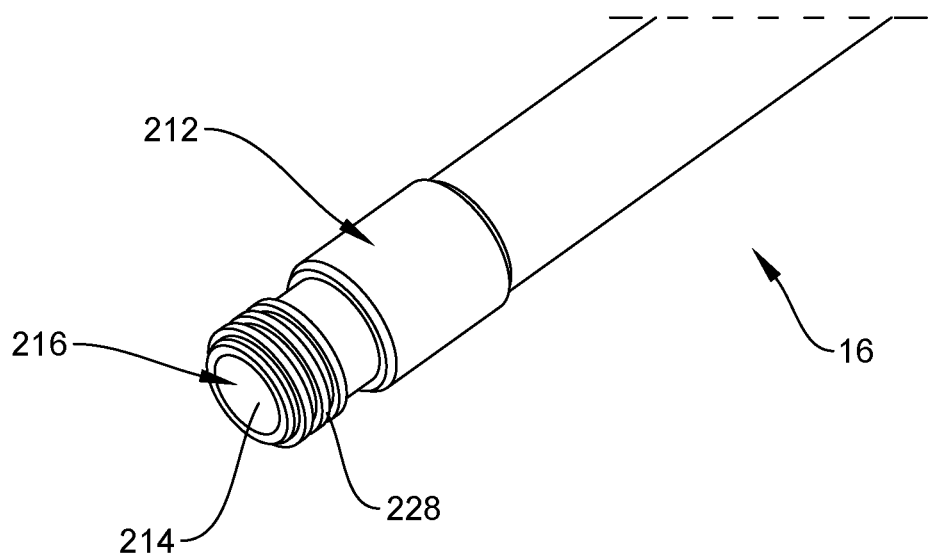
FIG. 17 is a perspective view of a portion of the component shown in FIG. 16.
Figure 18:
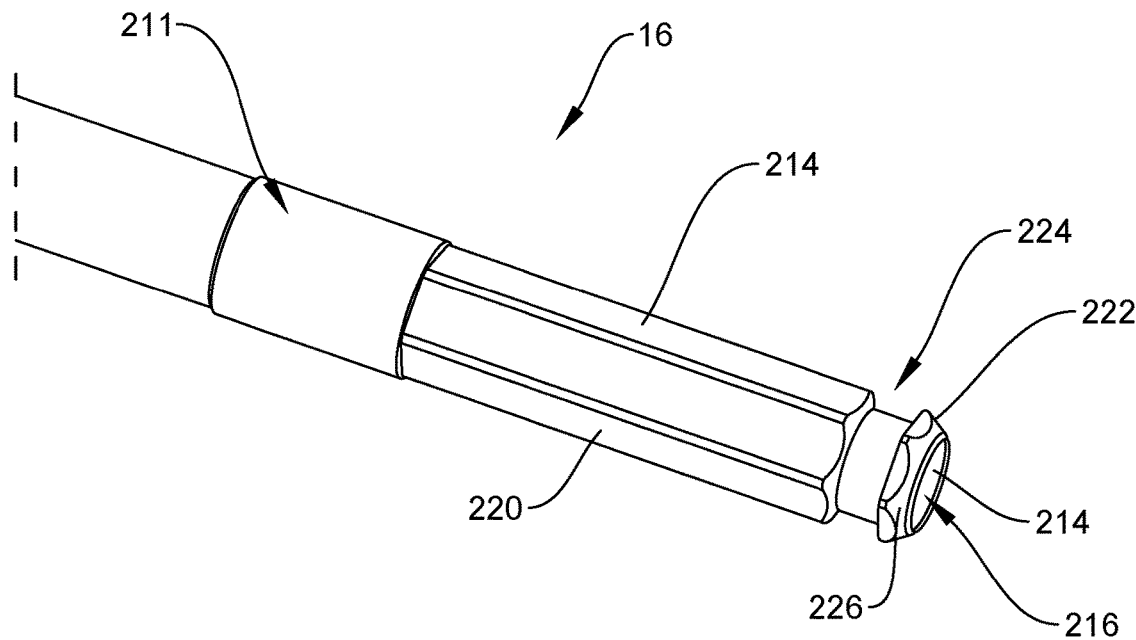
FIG. 18 is a perspective view of a portion of the component shown in FIG. 16.

Sleeve 16 is configured to be removably coupled to assembly 14 and includes a proximal end 211 and an opposite distal end 212, as shown in FIGS. 16-18, for example. Sleeve 16 includes an inner surface 214 defining a conduit 216 that extends through ends 211, 212. Shaft 194 is configured to be positioned in conduit 216 when sleeve 16 is coupled to assembly 14 such that end 211 is positioned in bore 78, as discussed herein. End 211 includes a wall 218 having an outer surface 220 that defines a hexagonal configuration and is configured for disposal in hexagonal bore 78 such that rotating sleeve 70 relative to sleeve 18 about axis X1 also rotates sleeve 16 relative to sleeve 18 about axis X1, as discussed herein. End 211 further includes a circumferential flange 222 that is spaced apart from wall 218 by a notch 224. That is, notch 224 defines a recess positioned between flange 222 and wall 218. In some embodiments, an outer surface of flange 222 defines a ramp 226 that is configured to slide along ramps 192 of latches 154, 160 as sleeve 16 is being coupled to assembly 14, as discussed herein. End 212 includes a threaded outer surface 228 configured to mate with a threaded inner surface 230 of arm 50 and a threaded inner surface 232 of arm 52 to couple sleeve 16 to receiver 54, as discussed herein.

Figure 19:
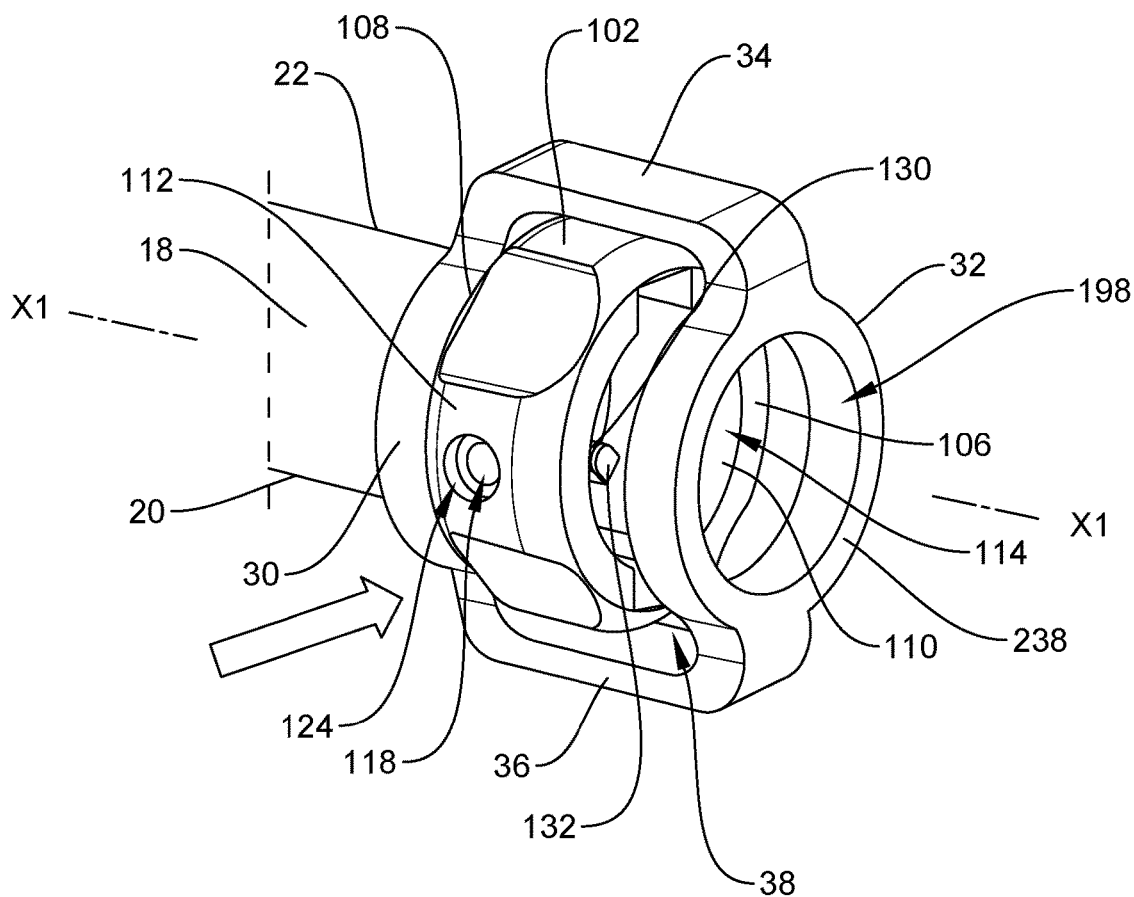
FIG. 19 is a perspective view of components of the surgical instrument shown in FIG. 1.
Figure 20:
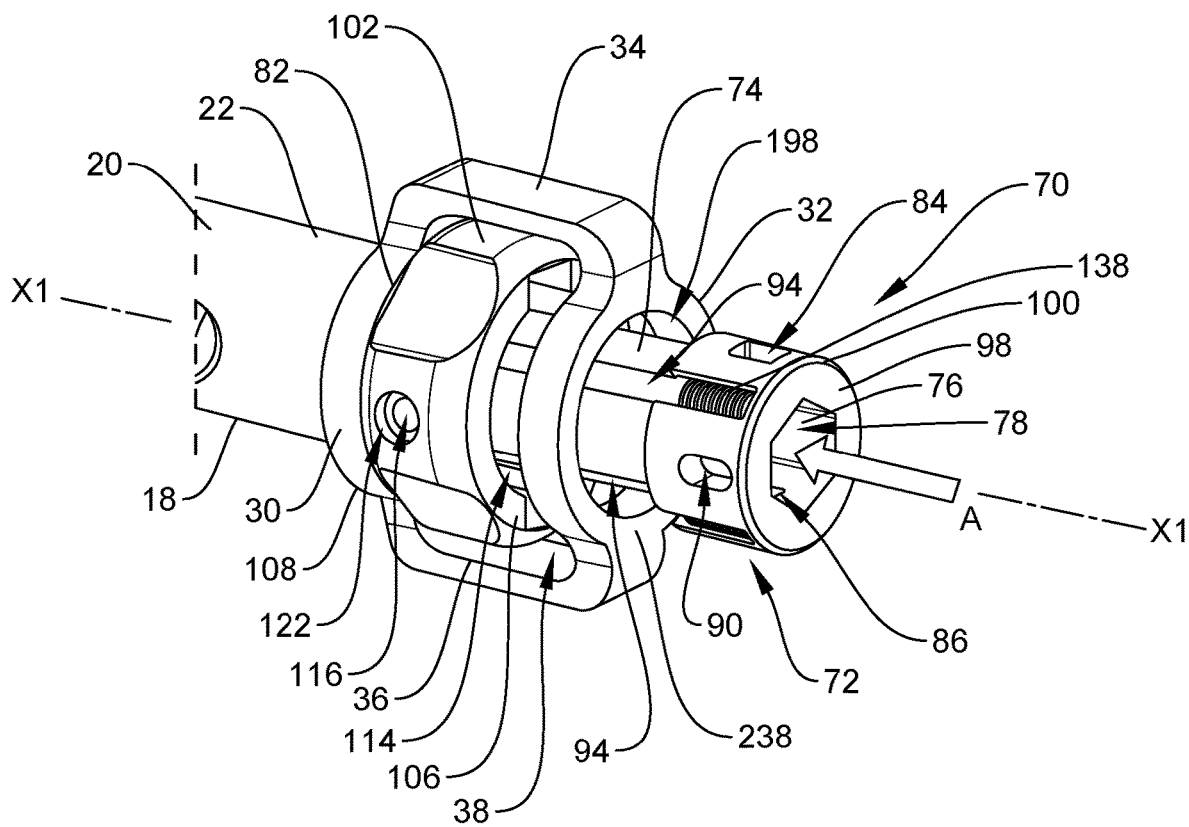
FIG. 20 is a perspective view of components of the surgical instrument shown in FIG. 1.
Figure 21:
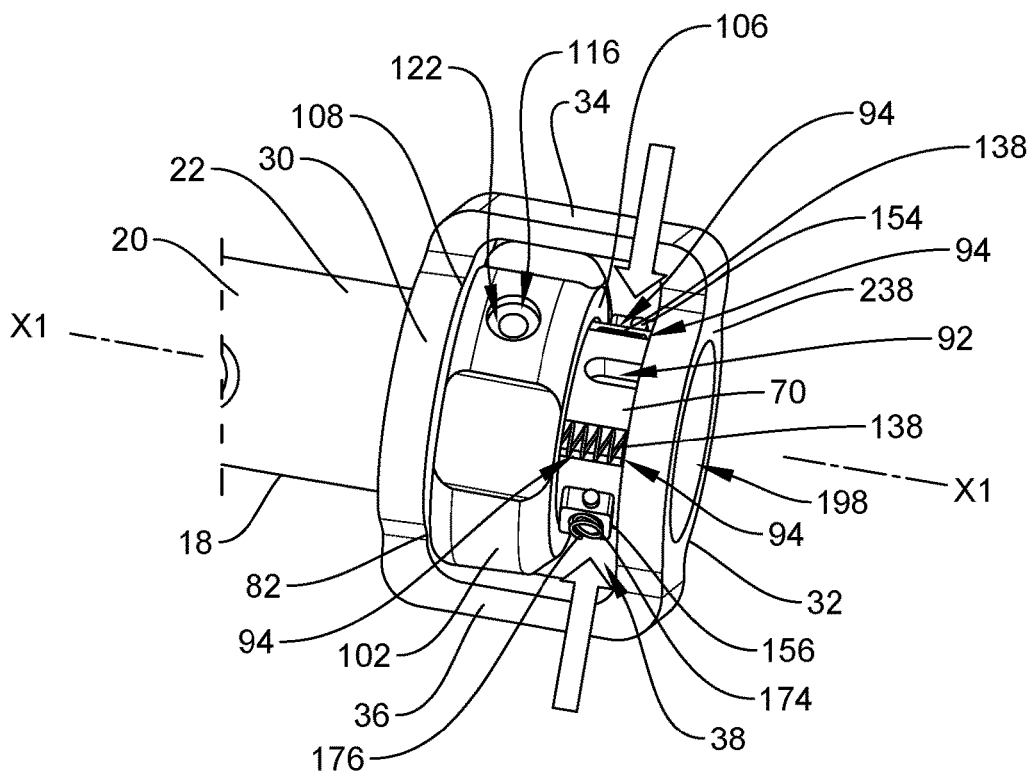
FIG. 21 is a perspective view of components of the surgical instrument shown in FIG. 1.
Figure 22:
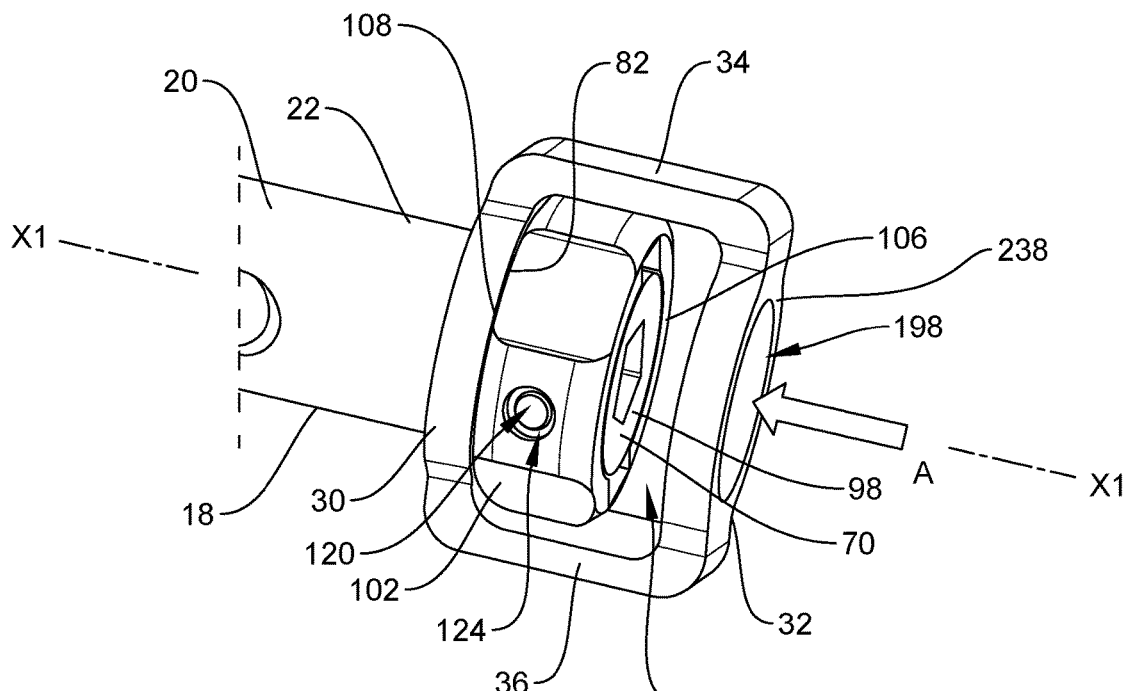
FIG. 22 is a perspective view of components of the surgical instrument shown in FIG. 1.
Figure 23:
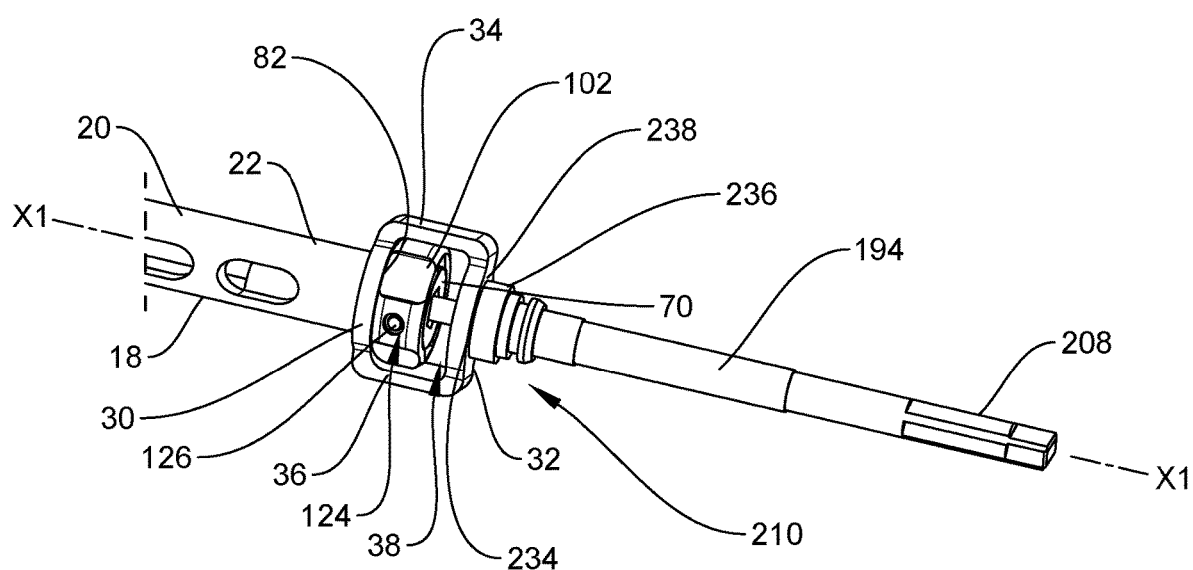
FIG. 23 is a perspective view of components of the surgical instrument shown in FIG. 1.

In some embodiments, assembly 14 is constructed by first inserting knob 102 into aperture 38 such that surface 108 of knob 102 directly engages surface 82 of plate 30 and channel 114 is coaxial with axis X1 and passageway 28, as shown in FIG. 19. Springs 138 are inserted into each of grooves 94 and sleeve 70 is inserted through opening 198 and into channel 114, as shown in FIG. 20. Sleeve 70 is then translated along axis X1 relative to sleeve 18 and knob 102 in the direction shown by arrow A in FIG. 20 until portion 72 of sleeve 70 is positioned entirely within aperture 38 and portion 74 of sleeve 70 is positioned in passageway 28, as shown in FIG. 21. Latch 154 is inserted into cavity 84 and latch 160 is inserted into cavity 86, as discussed herein, as also shown in FIG. 21. Sleeve 70 is then translated relative to sleeve 18 and knob 102 along axis X1 in the direction shown by arrow A in FIG. 20 such that ends 140 of springs 138 engage surfaces 132 of tabs 130 and surface 98 is flush with surface 106, as shown in FIG. 22. Shaft 194 is then coupled to sleeve 18, sleeve 70 and knob 102 by inserting end 200 through opening 198 and translating shaft 194 relative to sleeve 18, sleeve 70 and knob 102 in the direction shown by arrow A in FIG. 22 until tip 202 extends distal to tabs 42, 44 and a distal surface 234 of a flange 236 of shaft 194 directly engages a proximal surface 238 of plate 32, as shown in FIG. 23. Shaft 194 can then be welded to sleeve 18 to permanently fix shaft 194 relative to sleeve 18 and complete the construction of assembly 14 such that sleeve 16 is ready to be removably coupled to assembly 14, as discussed herein.

Figure 24:
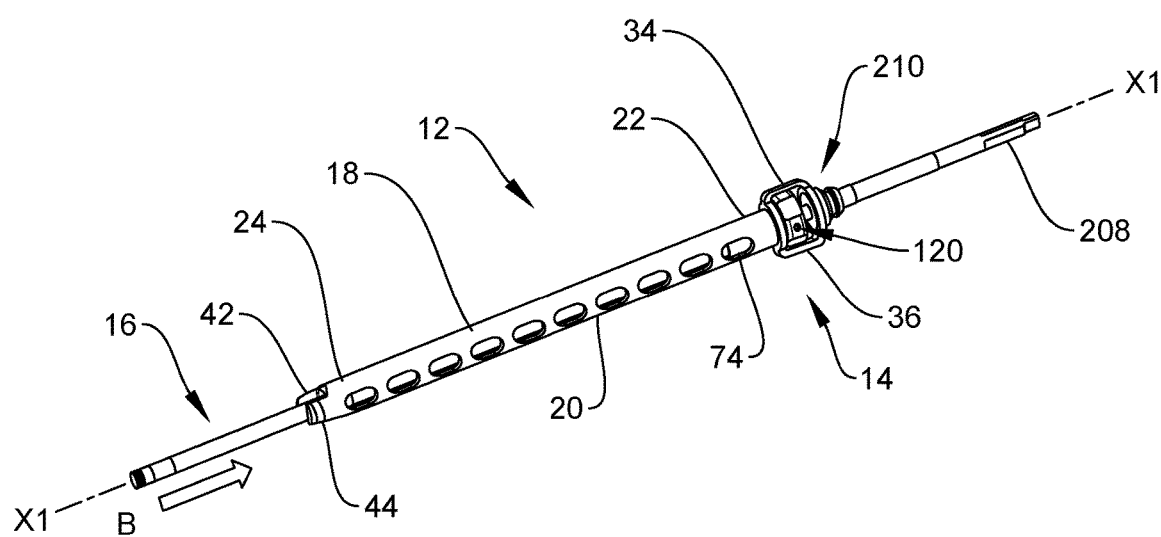
FIG. 24 is a perspective view of components of the surgical instrument shown in FIG. 1.
Figure 25:
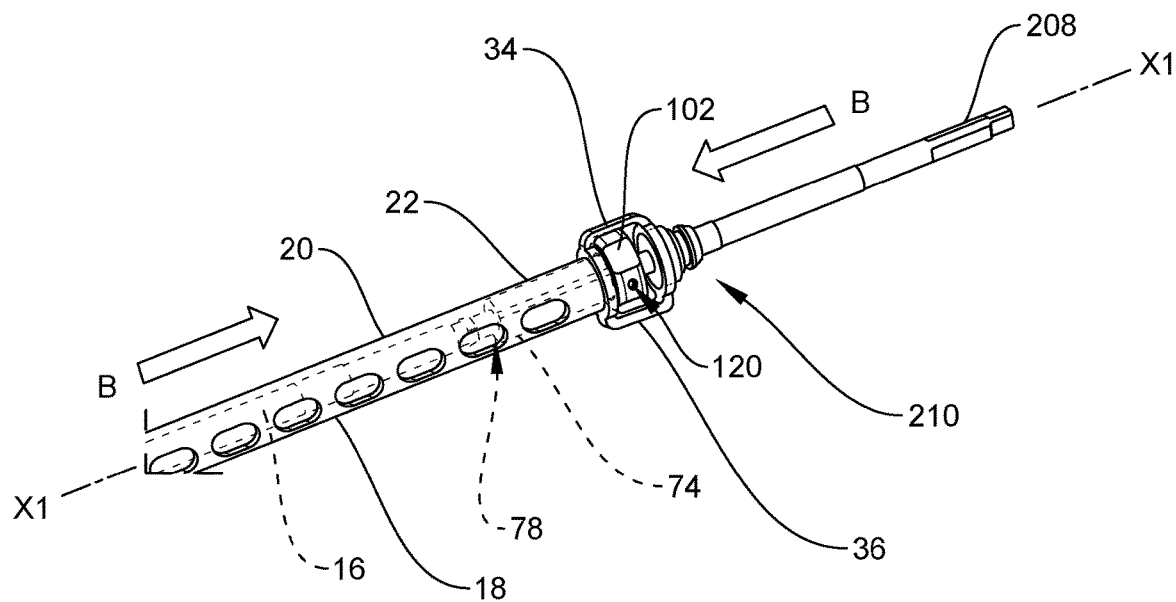
FIG. 25 is a perspective view, in part phantom, of components of the surgical instrument shown in FIG. 1.
Figure 26:
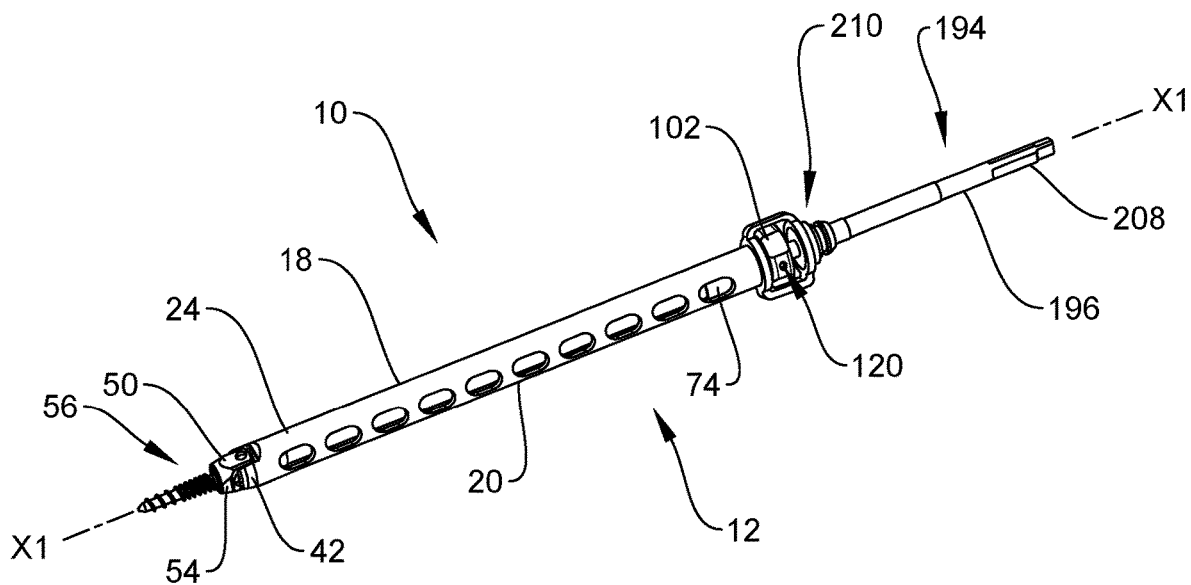
FIG. 26 is a perspective view of the surgical instrument shown in FIG. 1 coupled to the implant shown in FIG. 4.
Figure 27:
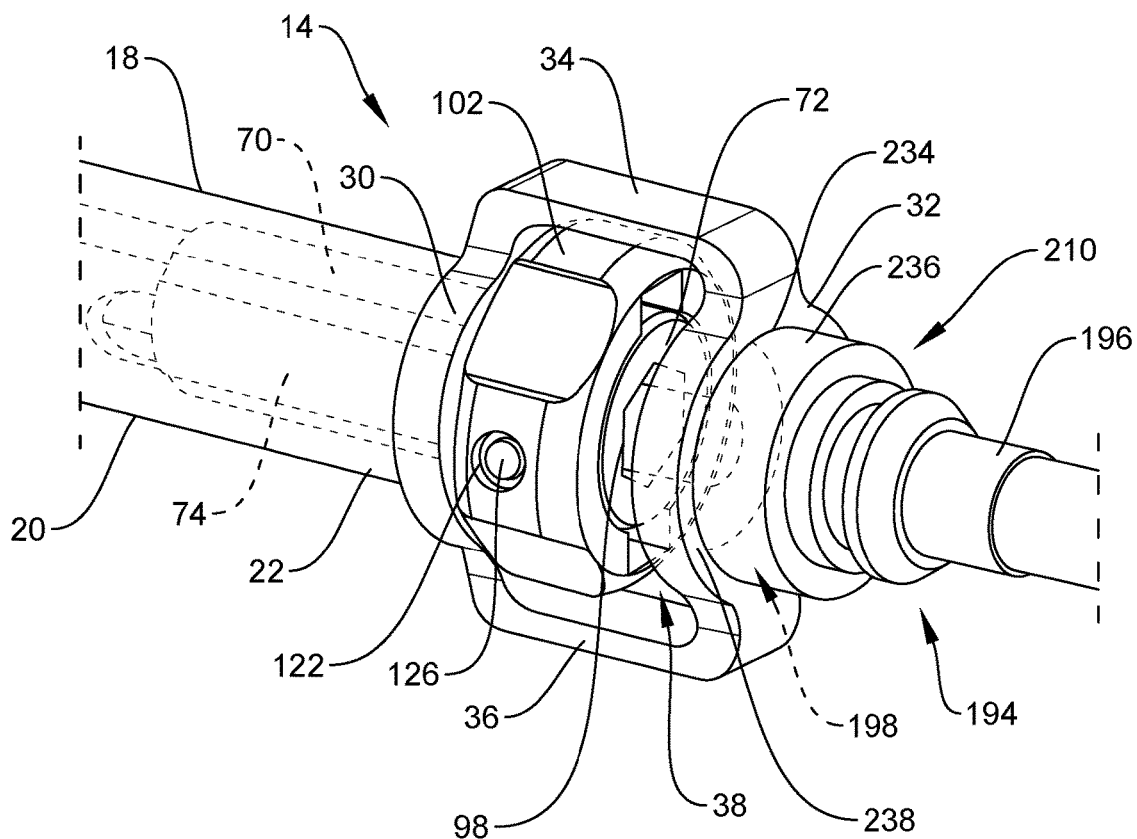
FIG. 27 is a perspective view, in part phantom, of components of the surgical instrument shown in FIG. 1.
Figure 28:
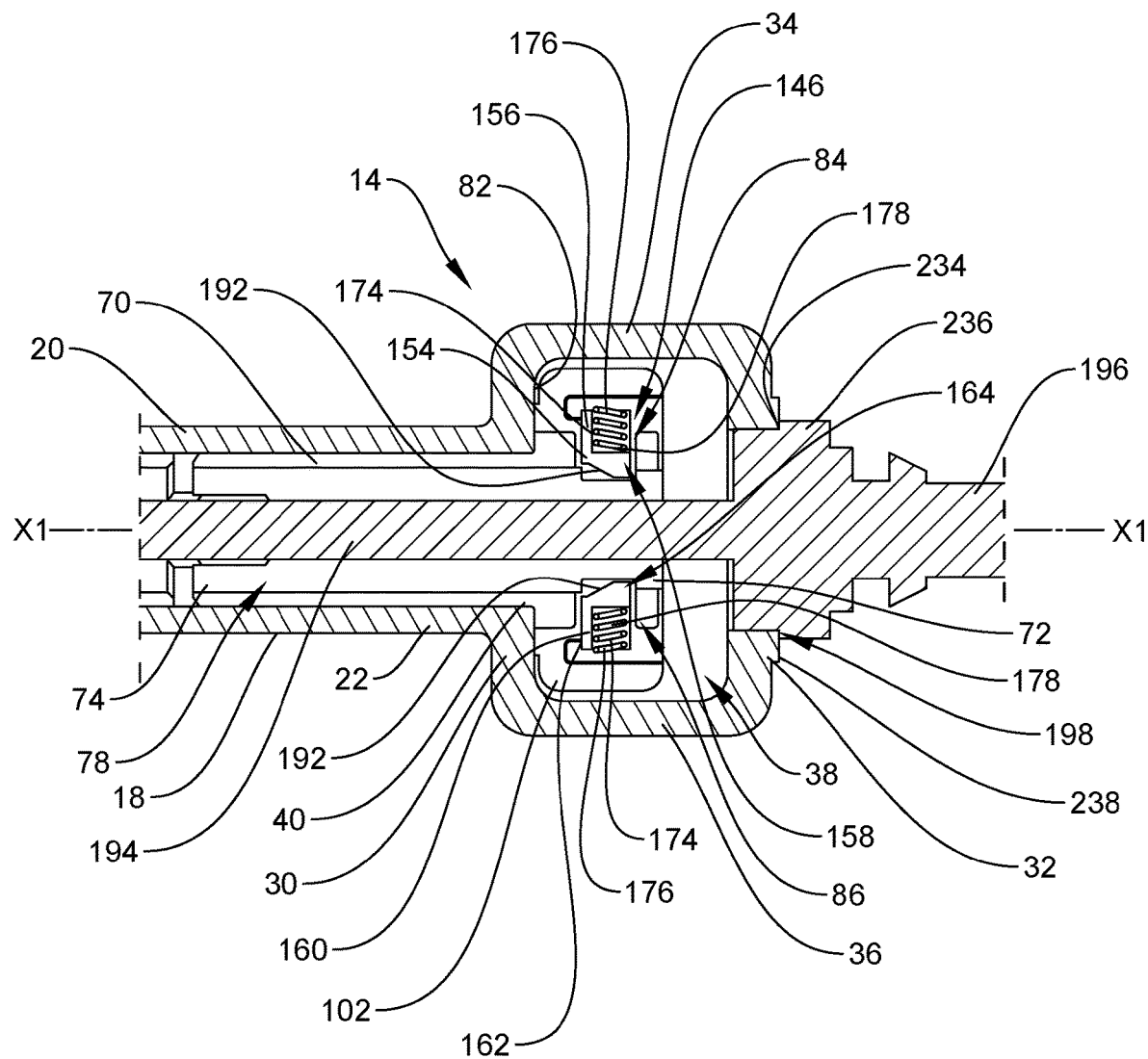
FIG. 28 is a side, cross-sectional view of components of the surgical instrument shown in FIG. 1.
Figure 30:
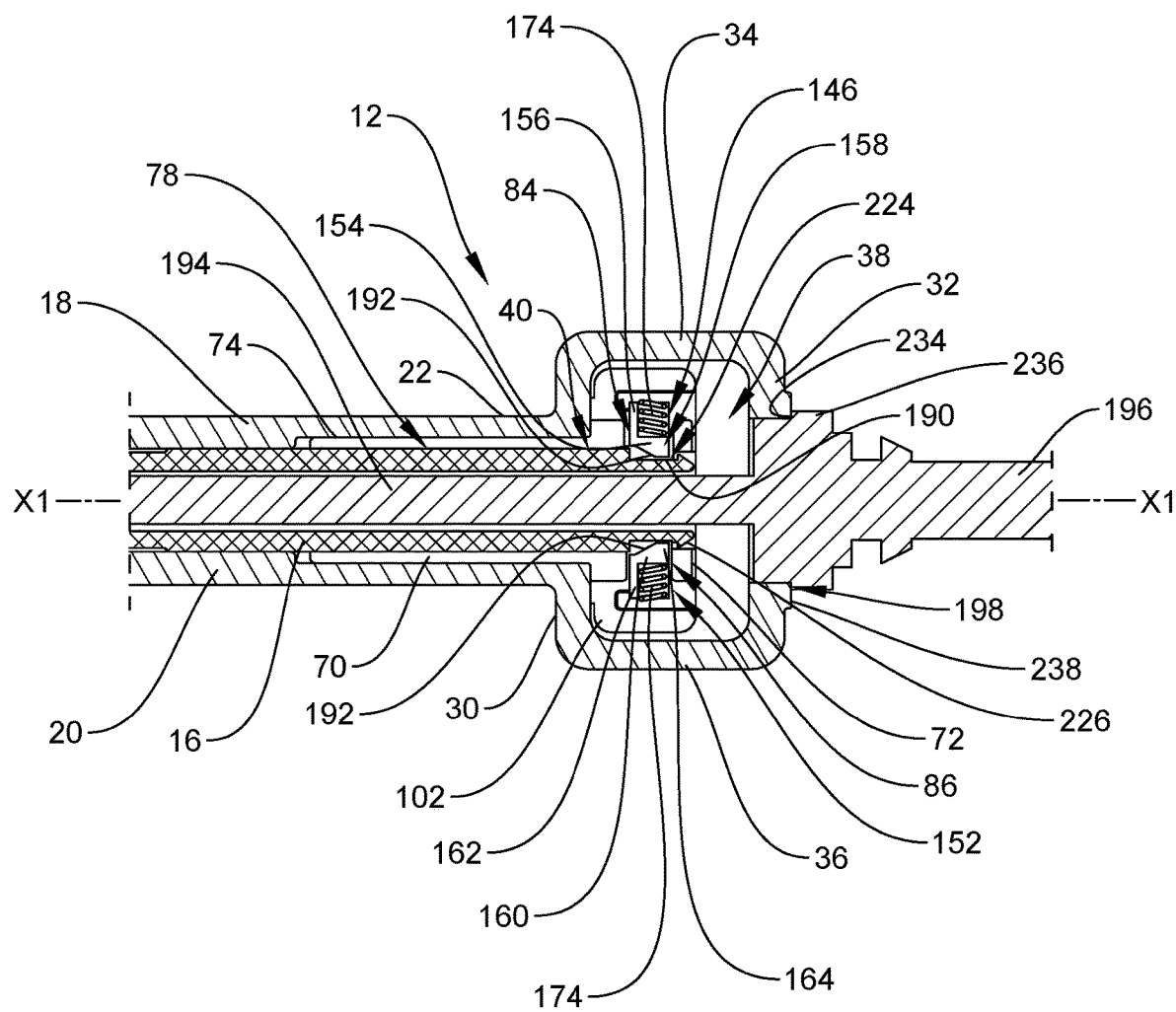
FIG. 30 is a side, cross-sectional view of a portion of the surgical instrument shown in FIG. 1.

In some embodiments, sleeve 16 is removably coupled to assembly 14 by inserting end 211 of sleeve 16 into passageway 28 such that shaft 194 is positioned in conduit 216 of sleeve 16 and translating sleeve 16 relative to assembly 14 in the direction shown by arrow B in FIG. 24. When sleeve 16 is positioned in passageway 28 such that shaft 194 is positioned in conduit 216 of sleeve 16 and sleeve 16 is spaced apart from sleeve 70, as shown in FIG. 25, driver 12 is in a first orientation. To move driver 12 from the first orientation, shown in FIGS. 24 and 25 to a second orientation, sleeve 16 is translated relative to assembly 14 in the direction shown by arrow B in FIG. 25 until wall 218 of sleeve 16 is positioned in bore 78 such that the hexagonal configuration defined by wall 218 mates with the hexagonal configuration defined by bore 78, as discussed herein. Knob 102 is translated relative to sleeve 18 along axis X1 in the direction shown by arrow A in FIG. 25 at the same time sleeve 16 is translated relative to assembly 14 in the direction shown by arrow B in FIG. 25 to snap sleeve 16 into place within assembly 14 such that latches 154, 160 are positioned in notch 224 of sleeve 16, as shown in FIG. 30 and discussed herein. Once sleeve 16 snaps into place within assembly 14, as shown in FIG. 30, sleeve 16 is prevented from translating relative to sleeve 18 along axis X1 and is ready for use to drive a bone screw, such as, for example, bone screw 56 into bone.

Figure 29:
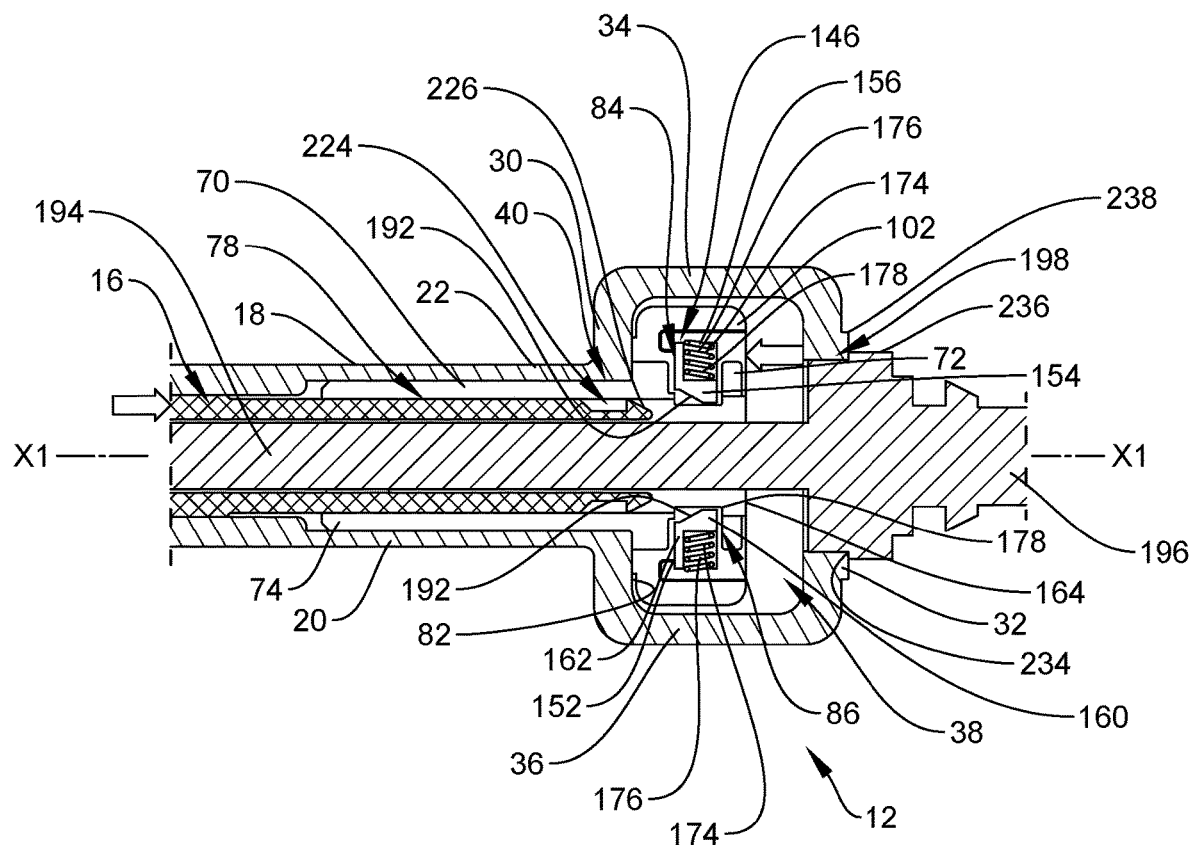
FIG. 29 is a side, cross-sectional view of a portion of the surgical instrument shown in FIG. 1.

In some embodiments, driver 12 moves from the first orientation, in which sleeve 16 is able to translate relative to sleeve 18 along axis X1, as shown in FIGS. 24 and 25, to the second orientation, shown in FIG. 30, in which sleeve 16 is snapped into place within assembly 14 by translating sleeve 16 relative to assembly 14 in the direction shown by arrow B in FIG. 25 after inserting end 211 of sleeve 16 into passageway 28 such that shaft 194 is positioned in conduit 216 of sleeve 16. Sleeve 16 is translated relative to assembly 14 in the direction shown by arrow B in FIG. 25 such that end 211 is positioned in bore 78, as shown in FIG. 29. At this point, latches 154, 160 are spaced apart from notch 224. That is, latches 154, 160 are not positioned in notch 224. Sleeve 16 is further translated relative to assembly 14 in the direction shown by arrow B in FIG. 25 such that ramps 192 ride along ramp 226. Sleeve 16 is further translated relative to assembly 14 in the direction shown by arrow B in FIG. 25 such that latches 154, 160 move into notch 224, as shown in FIG. 30, such that driver 12 is in the second orientation. The forces provided by springs 174 cause latches 154, 160 to move into notch 224 when latches 154, 160 are aligned with notch 224 and prevent translation of sleeve 16 relative to sleeve 18 along axis X1 when driver 12 is in the second orientation.

Figure 31:
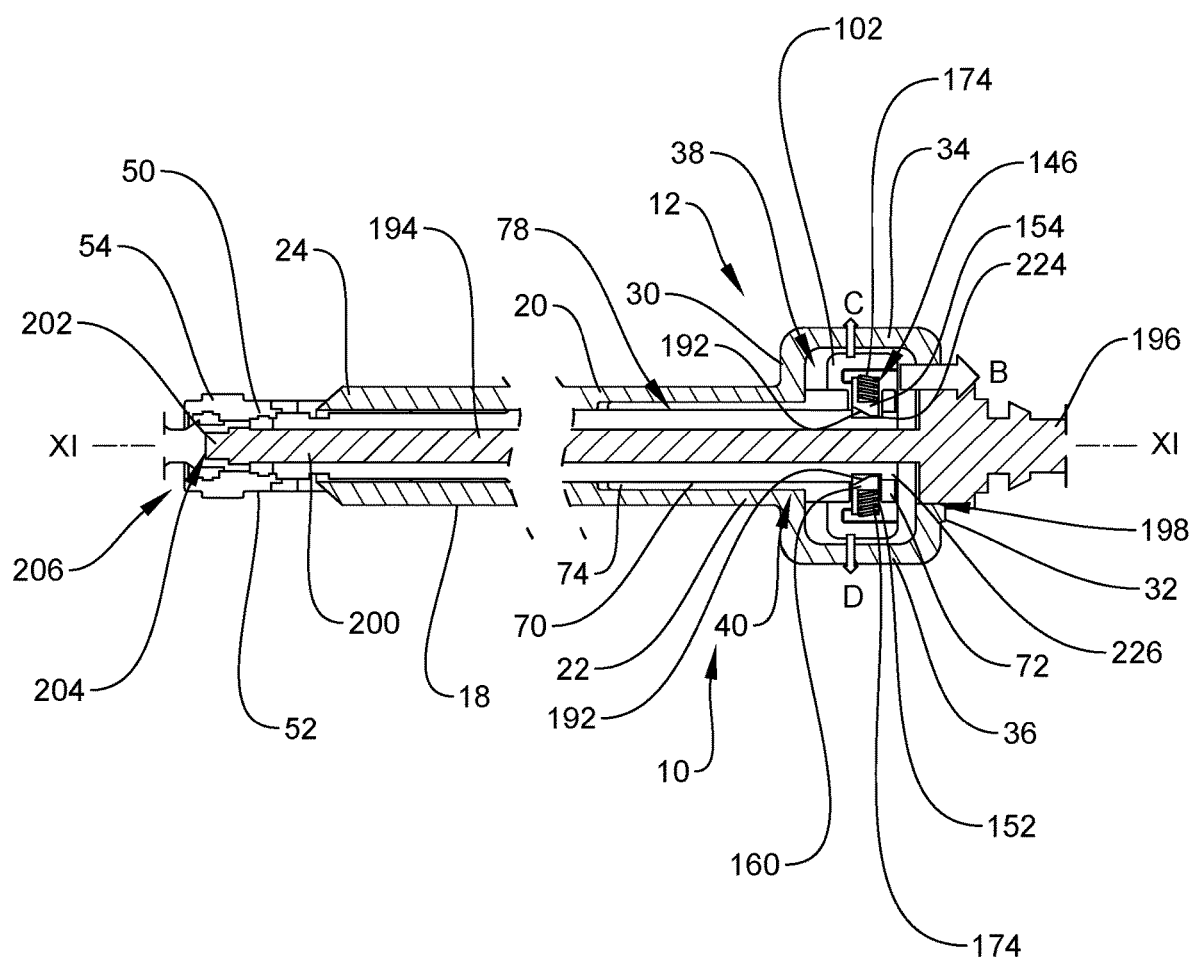
FIG. 31 is a breakaway side, cross-sectional view of the surgical instrument shown in FIG. 1 coupled to the implant shown in FIG. 4.
Figure 31A:
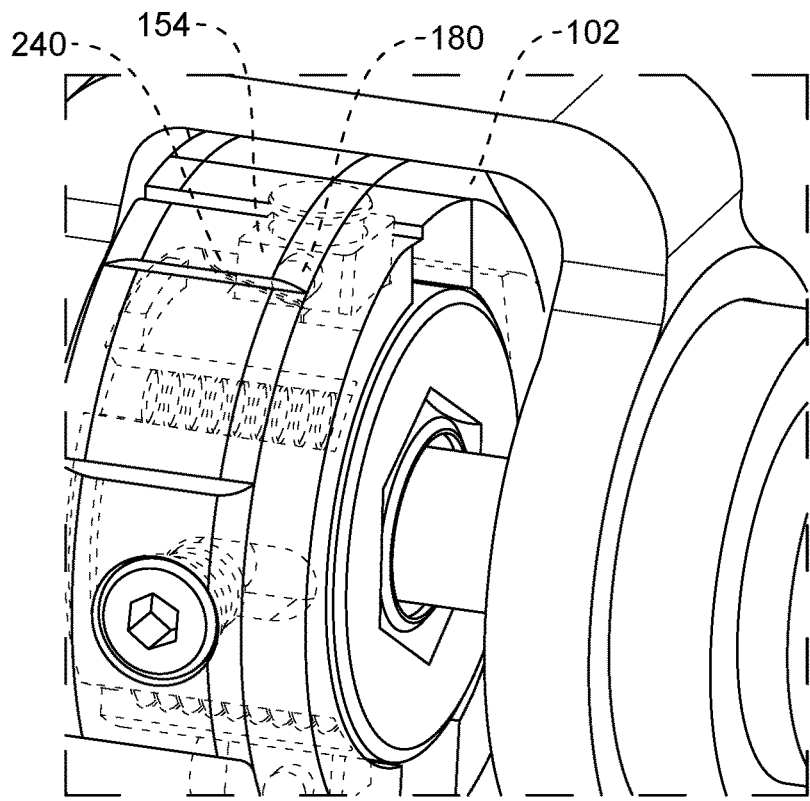
FIG. 31A is a perspective view, in part phantom, of the surgical instrument shown in FIG. 1.
Figure 31B:
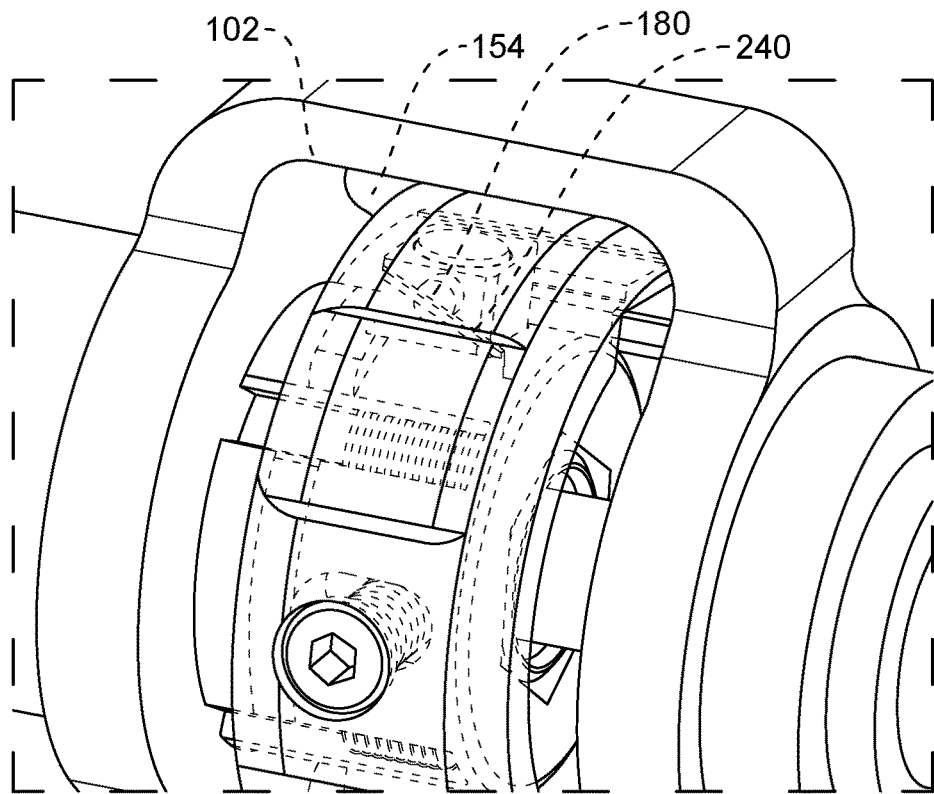
FIG. 31B is a perspective view, in part phantom, of the surgical instrument shown in FIG. 1.
Figure 32:
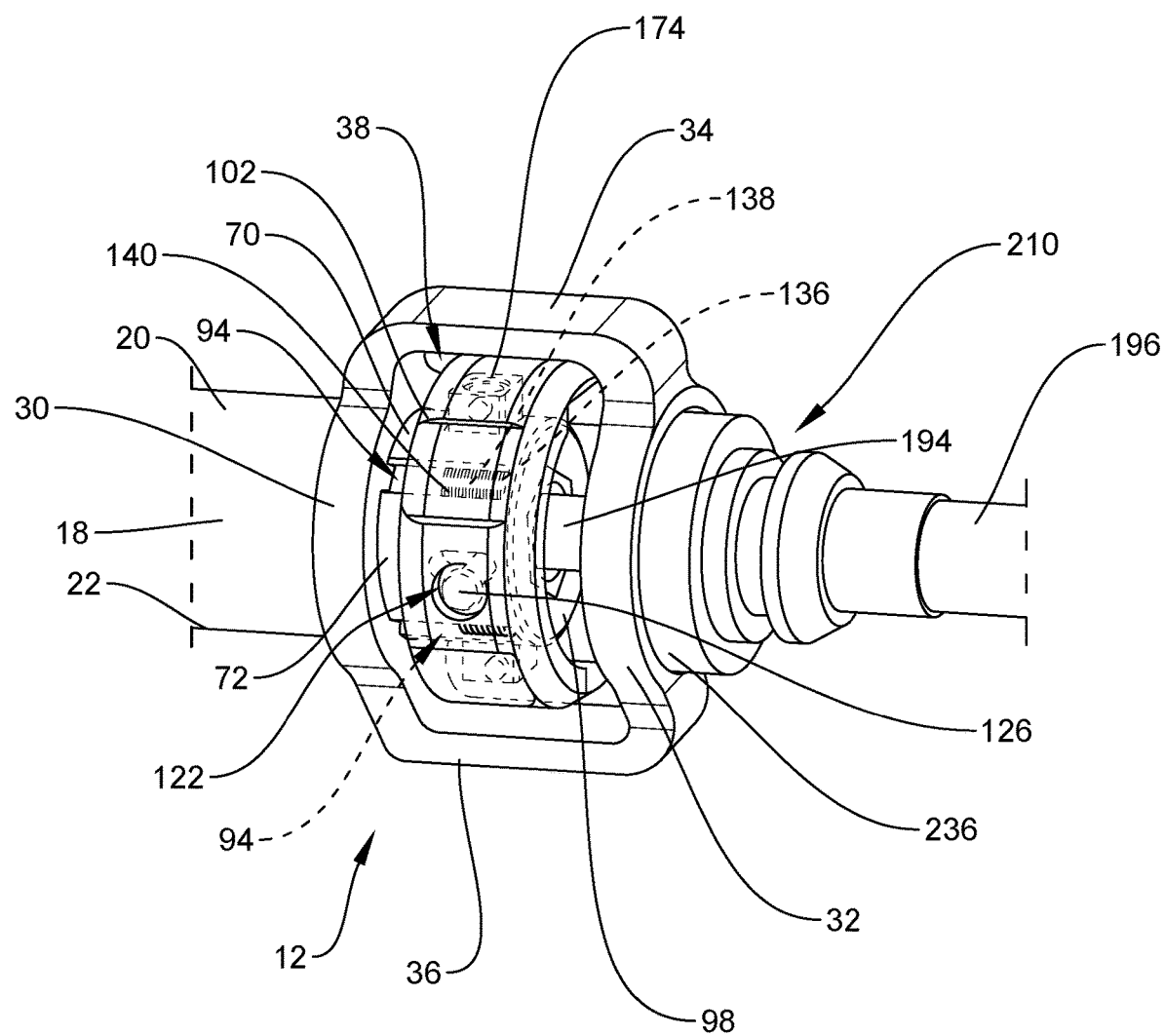
FIG. 32 is a perspective view, in part phantom, of the surgical instrument shown in FIG. 1.

Driver 12 is movable from the second orientation, shown in FIG. 30, in which sleeve 16 is prevented from translating relative to sleeve 18 along axis X1 to a third orientation, in which sleeve 16 is configured to translate relative sleeve 18 along axis X1 to allow for removal of sleeve 16 from assembly 14. In some embodiments, driver 12 moves from the second orientation, shown in FIG. 30, in which latches 154, 160 are positioned in notch 224 to the third orientation by moving knob 102 relative to sleeve 18 along axis X1 in the direction shown by arrow B in FIG. 31 such that pegs 180, 184 of each of latches 154, 160 ride up along ramps 240 of knob 102, as shown in FIGS. 31A and 31B, to move latch 154 relative to knob 102 and sleeve 70 in the direction shown by arrow C in FIG. 31 and move latch 160 relative to knob 102 and sleeve 70 in the direction shown by arrow D in FIG. 31 such that latches 154, 160 move out of notch 224 and allow sleeve 16 to be removed from assembly. Driver 12 is shown in the third orientation in FIGS. 31 and 32. Sleeve 70 remains stationary relative to sleeve 18 as driver 12 moves from the second orientation, shown in FIG. 30 to the third orientation, shown in FIGS. 31 and 32. That is, sleeve 70 is in the same position relative to sleeve 18 when driver is in both the second and third orientations.

Figure 33:
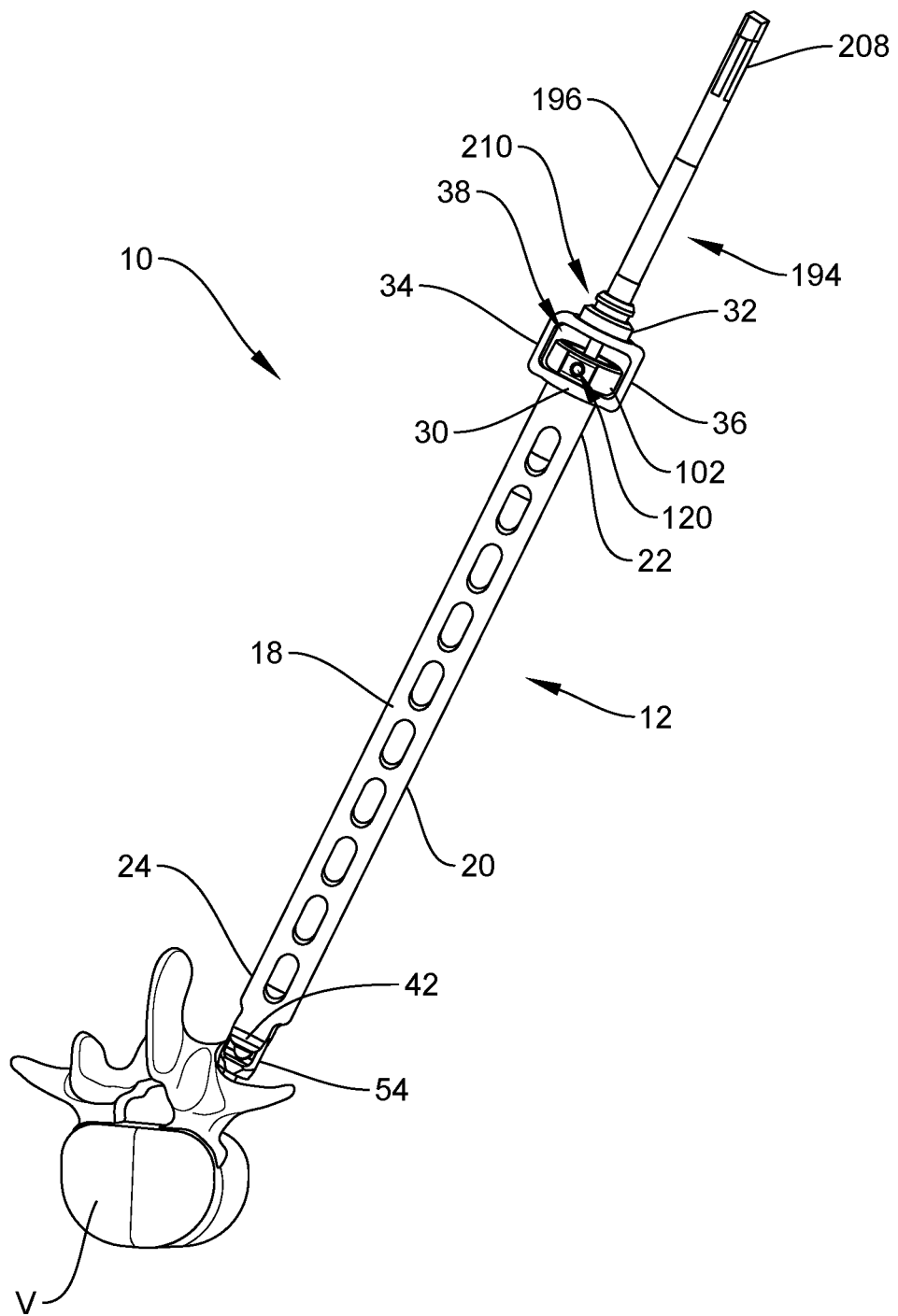
FIG. 33 is a plan view of the surgical instrument shown in FIG. 1 coupled to the implant shown in FIG. 4.
Figure 34:
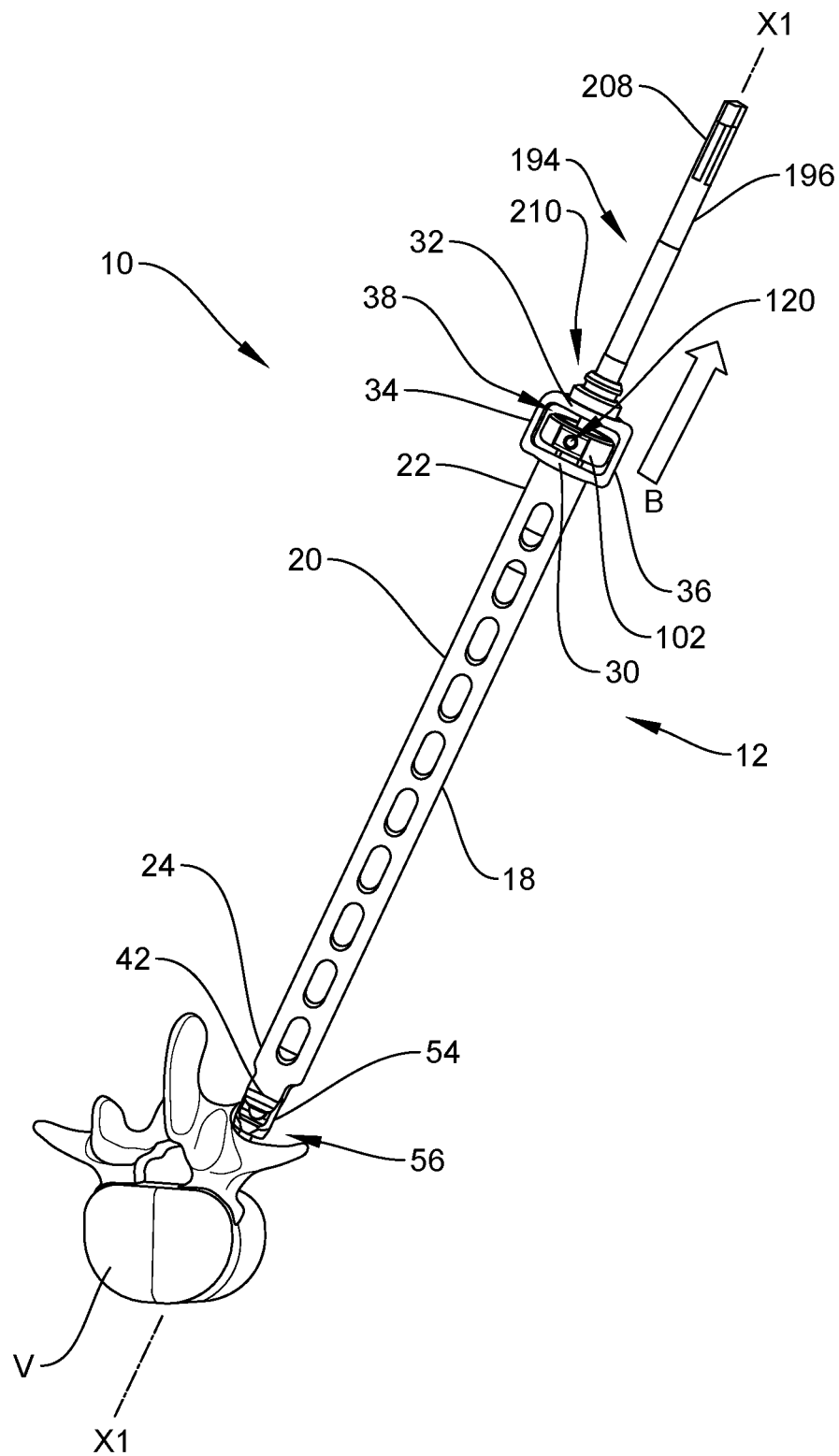
FIG. 34 is a plan view of the surgical instrument shown in FIG. 1 coupled to the implant shown in FIG. 4.
Figure 35:
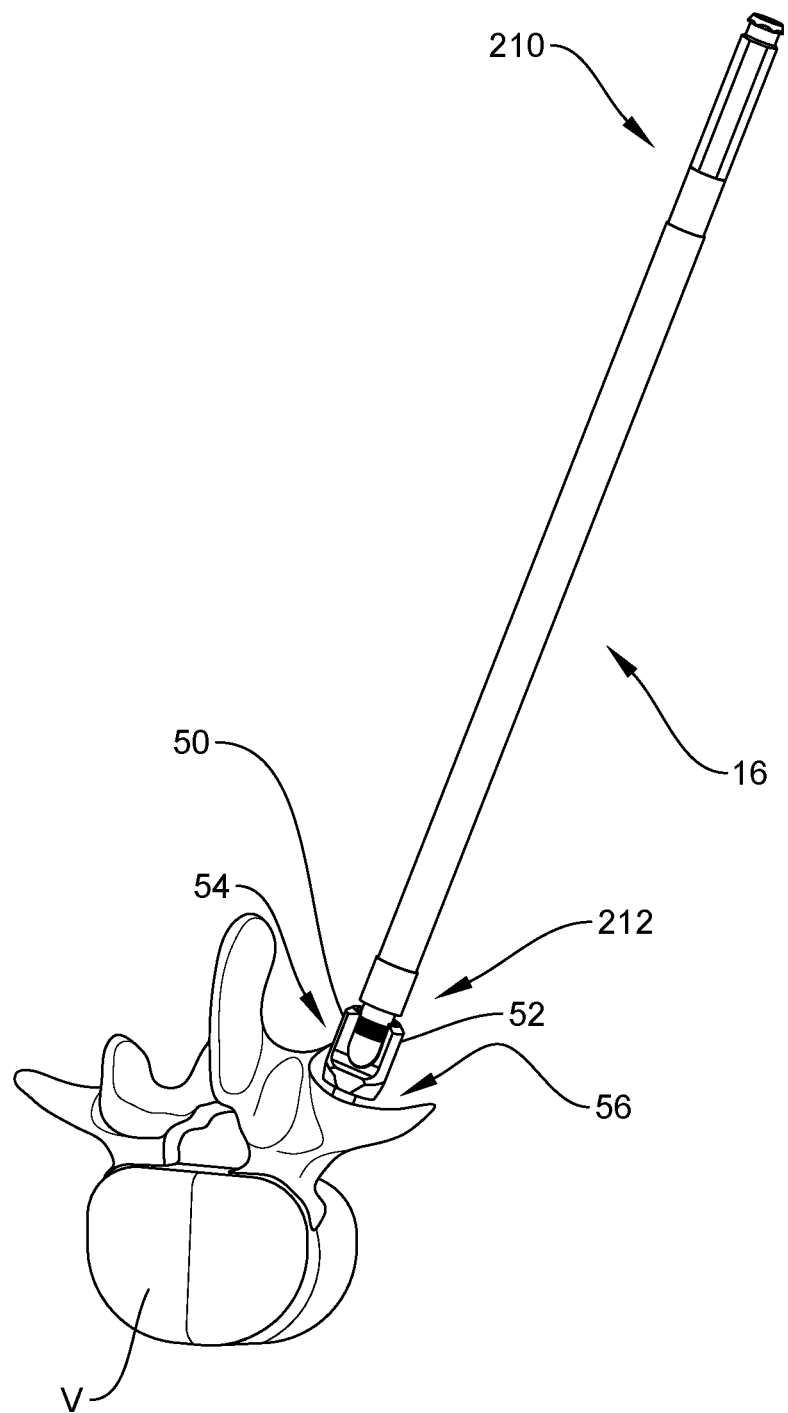
FIG. 35 is a plan view of a component of the surgical instrument shown in FIG. 1 coupled to the implant shown in FIG. 4.
Figure 36:
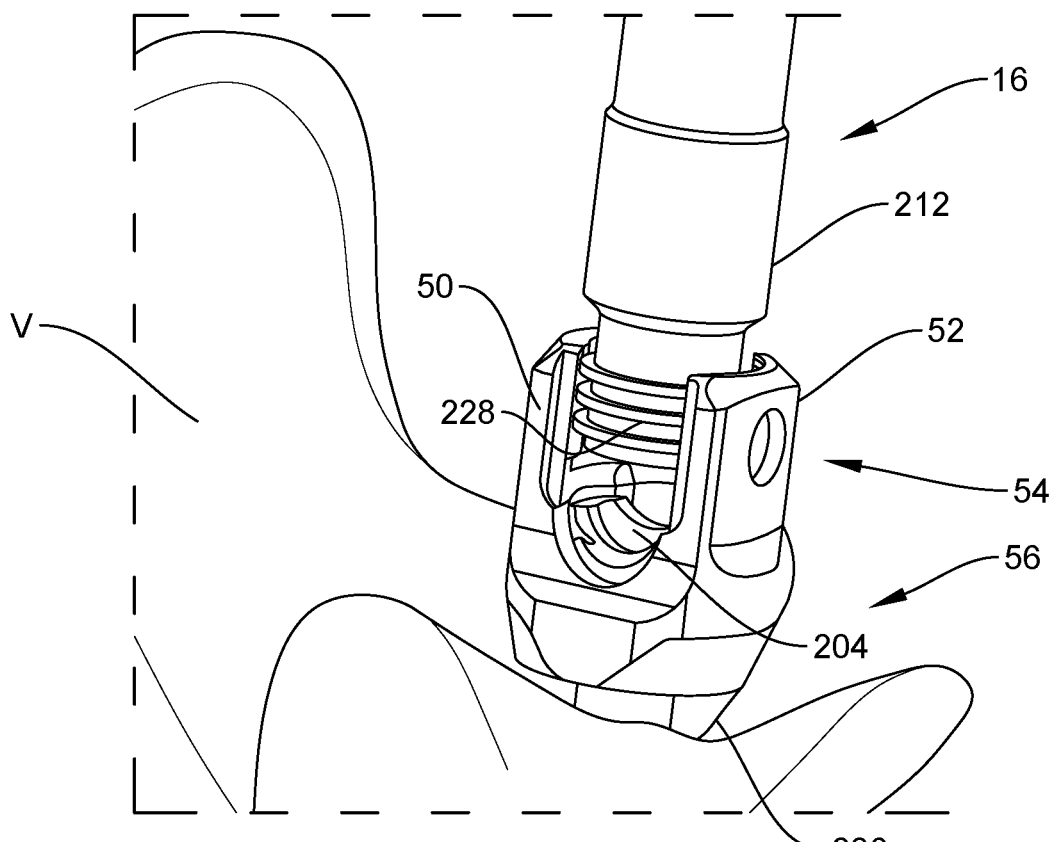
FIG. 36 is a plan view of a component of the surgical instrument shown in FIG. 1 coupled to the implant shown in FIG. 4.
Figure 37:
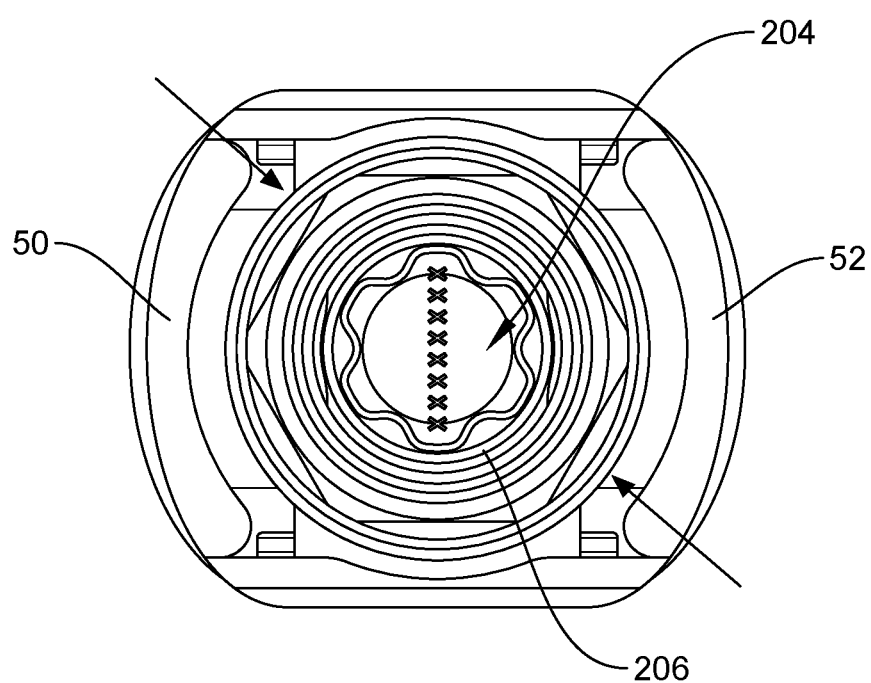
FIG. 37 is a top view of a component of the surgical instrument shown in FIG. 1 and the implant shown in FIG. 4.

In use, bone screw 56 is connected with driver 12 when driver 12 is in the second orientation, in which sleeve 16 is prevented from translating relative to sleeve 18 along axis X1, by inserting tip 202 into socket 204 such that threaded surface 228 of sleeve 16 is aligned with threaded surfaces 230, 232 of arms 50, 52, tabs 42, 44 are positioned between arms 50, 52, arm 50 is positioned in recess 46 and arm 52 is positioned in recess 48, as shown in FIG. 33. Knob 102 is rotated relative to sleeve 18 about axis X1 to rotate sleeve 16 to mate threaded surface 228 with threaded surfaces 230, 232 and couple sleeve 16 with receiver 54. Driver 12 is then rotated about axis X1 to simultaneously rotate receiver 54 and shaft 206 about axis X1 and drive shaft 206 into tissue, such as, for example, bone. Assembly 14 may then be moved from bone screw 56 by moving driver 12 from the second orientation shown in FIG. 30, in which sleeve 16 is prevented from translating relative to sleeve 18 along axis X1, to the third orientation shown in FIGS. 31 and 32, in which sleeve 16 is capable of translating relative to sleeve 18 along axis X1. Once driver 12 is in the third orientation, assembly 14 can be disengaged from bone screw 56 by moving assembly 14 proximally relative to sleeve 16 to disengage assembly 14 from bone screw 56, while leaving sleeve 16 coupled to bone screw 56, as shown in FIGS. 35 and 36.

In assembly, operation and use, spinal implant system 10, similar to the systems and methods described herein, is employed with a surgical procedure, such as, for example, a treatment of an applicable condition or injury of an affected section of a spinal column and adjacent areas within a body. In some embodiments, one or all of the components of spinal implant system 10 can be delivered or utilized as a pre-assembled device or can be assembled in situ. For example, in some embodiments, driver 12 may be delivered with driver 12 in the first orientation, in which sleeve 16 is not coupled to assembly 14. In some embodiments, driver 12 may be delivered with driver in the second orientation, in which sleeve 16 is coupled to assembly 14 such that sleeve 16 is prevented from translating relative to sleeve 18 along axis X1. Spinal implant system 10 may be completely or partially revised, removed or replaced.

In use, to treat one or more vertebrae, such as, for example, vertebra V1 shown in FIGS. 33-36, a medical practitioner obtains access to a surgical site in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby the vertebrae is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of the vertebrae as well as for aspiration and irrigation of a surgical region.

A pilot hole (not shown) is made in vertebra V1 for receiving shaft 206 of bone screw 56. Bone screw 56 is connected with driver 12, as described herein, and shown in FIG. 33, for example. In some embodiments, an actuator, such as, for example, a drill is coupled to portion 208 of shaft 194 to rotate driver 12 relative to vertebra V1 about axis X1 such that sleeve 16, sleeve 18 and shaft 194 rotate relative to vertebra V1 about axis X1. Rotation of driver 12 about axis X1 relative to vertebra V1 engages one or more threads of shaft 206 with vertebra V1 to fix shaft 206 relative to vertebra V1.

Once shaft 206 is sufficiently driven into vertebra V1 using driver 12, assembly 14 may be removed from bone screw 56, while leaving sleeve 16 attached to receiver 54 of bone screw 56, as discussed herein. In particular, the surgeon may grasp knob 102 by hand and translate knob 102 relative to sleeve 18 along axis X1 in the direction shown by arrow B in FIG. 34 while pulling back on sleeve 18 in the direction shown by arrow A in FIG. 34 to move driver 12 from the second orientation, in which sleeve 16 is prevented from translating relative to sleeve 18 along axis X1, to the third orientation, in which sleeve 16 is able to translate relative to sleeve 18 along axis X1. With driver 12 in the third orientation, assembly 14 is translated relative to sleeve 16 and bone screw 56 in the direction shown by arrow B in FIG. 34, leaving sleeve 16 coupled to receiver 54 of bone screw 56, as shown in FIGS. 35 and 36. In some embodiments, the surgeon may utilize sleeve 16 to guide other instruments, for example, to bone screw 56.

In some embodiments, sleeve 16 is coupled to screw 56 such that the maximum outside diameter of sleeve 16 is smaller than the maximum outside diameter of receiver 54 (and smaller than engagement slots of receiver 54). This allows instruments to slide down sleeve 16 and engage with those features so as to lock onto receiver 54.

Figure 38:
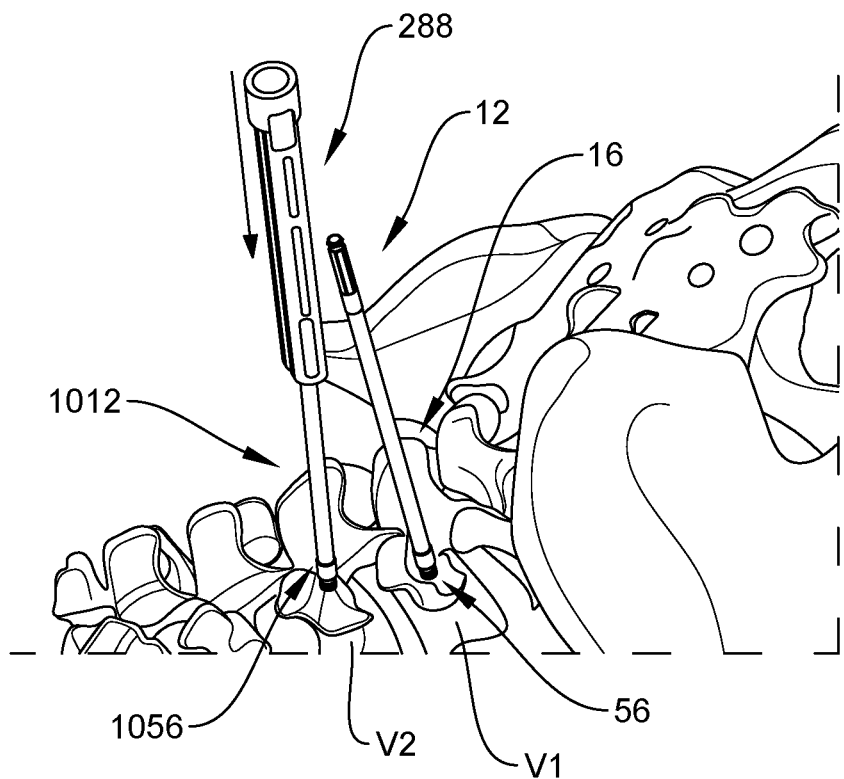
FIG. 38 is plan view of a component of the surgical instrument shown in FIG. 1 and a component of a second one of the surgical instruments shown in FIG. 1 coupled to a portion of an additional surgical instrument in accordance with the principles of the present disclosure.
Figure 39:
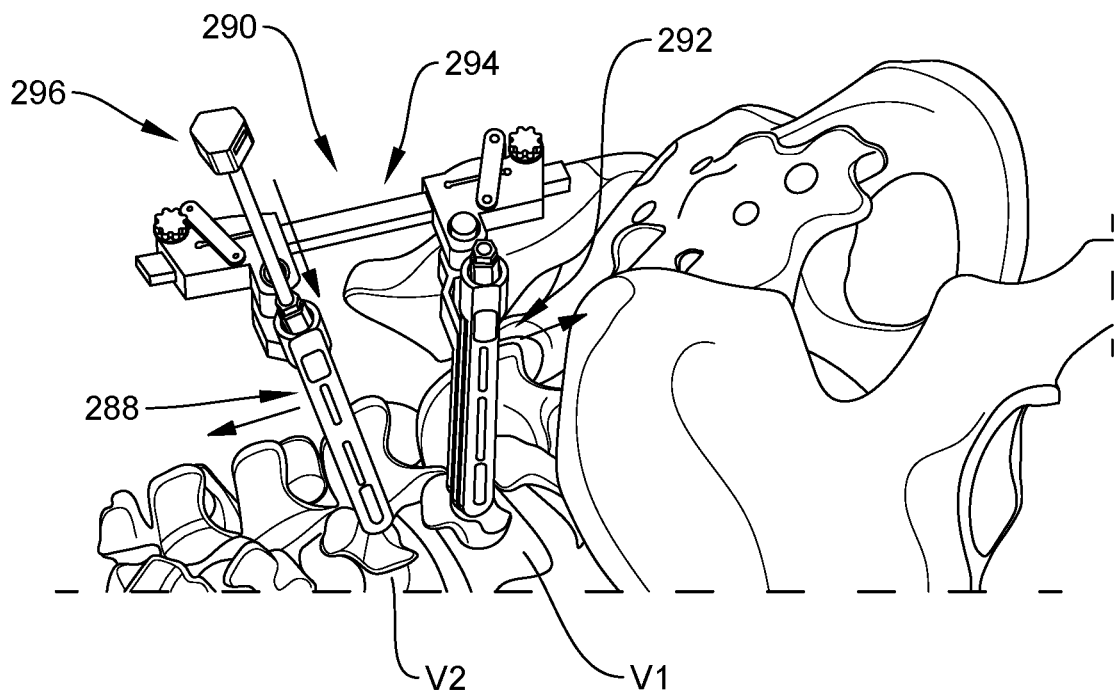
FIG. 39 is plan view of a component of the surgical instrument shown in FIG. 1 coupled to a component of the additional surgical instrument and a component of the second one of the surgical instruments shown in FIG. 1 coupled to the portion of the additional surgical instrument.
Figure 39A:
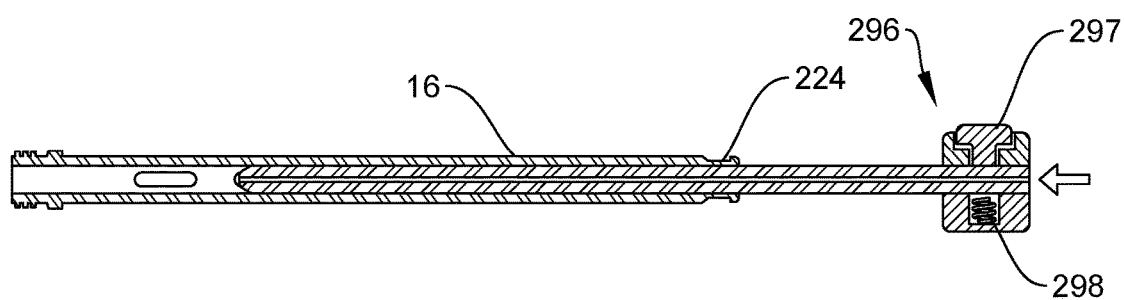
FIG. 39A is plan view of a component of the surgical instrument shown in FIG. 1 coupled to a component of the additional surgical instrument.
Figure 39B:
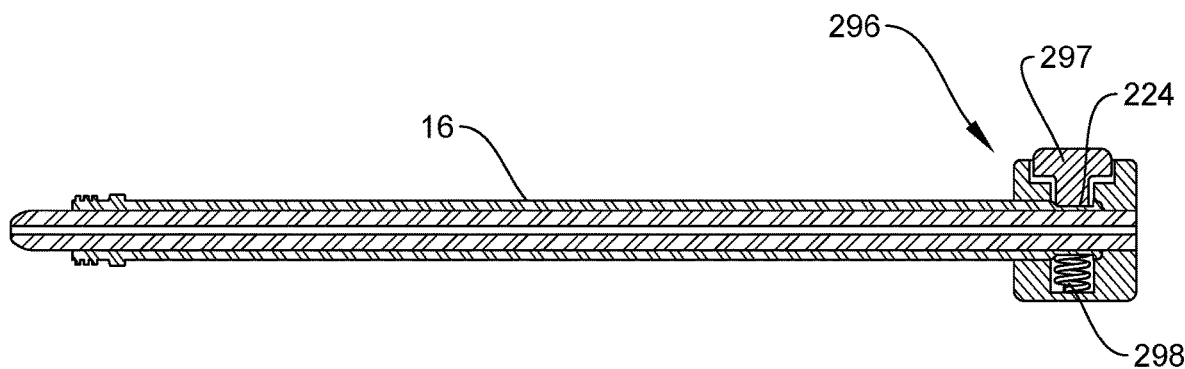
FIG. 39B is plan view of a component of the surgical instrument shown in FIG. 1 coupled to a component of the additional surgical instrument.

In some embodiments, driver 12 is used to drive bone screw 56 into vertebra V1, while retaining sleeve 16 coupled to bone screw 56 after assembly 14 has been removed from bone screw, and while another driver 1012, that is the same or similar to driver 12 is used to drive another bone screw 1056, that is the same or similar to bone screw 56, into a vertebra V2 that is adjacent to vertebra V1 in a patient's vertebrae, as shown in FIG. 38. In particular, driver 1012 may be used to drive bone screw 1056 into vertebra V2, while leaving sleeve 16 coupled to bone screw 1056 after assembly 14 has been removed from sleeve 16 in the same manner that driver 12 is used to drive bone screw 56 into vertebra V1, while leaving sleeve 16 coupled to bone screw 56 after assembly 14 has been removed from sleeve 16. A component of another instrument of system 10, such as, for example, a first tower 288 of an instrument 290 may be translated over sleeve 16 of driver 1012, while sleeve 16 of driver 1012 is coupled to bone screw 1056, as shown in FIG. 38. A second tower 292 of instrument 290 is translated over sleeve 16 of driver 12, while sleeve 16 of driver 12 is coupled to bone screw 56, as shown in FIG. 39. Tower 292 is coupled to tower 288 by a member 294 that allows relative movement between tower 288 and tower 292 and to maintain towers 288, 292 in place to selectively position tower 288 relative to tower 292. In some embodiments, sleeve 16 of driver 1012 is coaxial with tower 288 and sleeve 16 of driver 12 is coaxial with tower 292.

Tower 292 may be moved apart from tower 288 to create a working space for a give surgical procedure. A head locker 296 may be inserted through conduit 216 of driver 1012, as shown in FIG. 39, and/or the same or different head locker 296 may be inserted through conduit 216 of driver 12 to maintain the relative positioning of shank 54 of bone screw 1056 relative to receiver 54 of bone screw 1056 and/or the relative positioning of shank 206 of bone screw 56 relative to receiver 54 of bone screw 56 and create a rigid construction. In some embodiments, head locker 296 engages sleeve 16 of driver 1012 such that threads of head locker 296 engage threads of sleeve 16 of driver 1012 to couple head locker 296 to driver 1012 and/or head locker 296 engages sleeve 16 of driver 12 such that threads of head locker 296 engage threads of sleeve 16 of driver 12 to couple head locker 296 to driver 12. In some embodiments, head locker 296 disengages sleeve 16 of driver 1012 by pressing a button 297 on head locker 296 to uncouple head locker 296 from driver 1012 and/or head locker 296 disengages sleeve 16 of driver 12 by pressing button 297 to uncouple head locker 296 from driver 12. In particular, head locker 296 is introduced into sleeve 16 from the proximal end and button 297 causes a spring 298 to move into notch 224. When button 297 is pushed in, spring 298 is spaced apart from notch 224 and head locker 296 can be released from sleeve 16. Head locker 296 is biased to a locked position when any force that was applied to button 297 is released such spring 298 moves into notch 224 to prevent head locker 296 from being released from sleeve 16. In some embodiments, head locker 296 includes a wall having a hexagonal configuration that engages a portion of sleeve 16 also having a hexagonal configuration, such as, for example, outer surface 220 such that rotation of head locker 296 also rotates sleeve 16 to further thread until the head is locked.

In some embodiments, inserting head locker 296 into conduit 216 of driver 1012 while sleeve 16 of driver 1012 is coupled to bone screw 1056 prevents movement of receiver 54 of bone screw 1056 relative to shank 206 of bone screw 1056 and/or inserting head locker 296 into conduit 216 of driver 12 while sleeve 16 of driver 12 is coupled to bone screw 56 prevents movement of receiver 54 of bone screw 56 relative to shank 206 of bone screw 56. In some embodiments, inserting head locker 296 into conduit 216 of driver 1012 while sleeve 16 of driver 1012 is coupled to bone screw 1056 prevents movement of receiver 54 of bone screw 1056 relative to shank 206 of bone screw 1056 by pressing a crown of bone screw 1056 against shank 206 of bone screw 1056 in a manner that prevents movement of receiver 54 of bone screw 1056 relative to shank 206 of bone screw 1056 and/or inserting head locker 296 into conduit 216 of driver 12 while sleeve 16 of driver 12 is coupled to bone screw 56 prevents movement of receiver 54 of bone screw 56 relative to shank 208 of bone screw 56 by pressing a crown of bone screw 56 against shank 206 of bone screw 56 in a manner that prevents movement of receiver 54 of bone screw 56 relative to shank 206 of bone screw 56.

Figure 40:
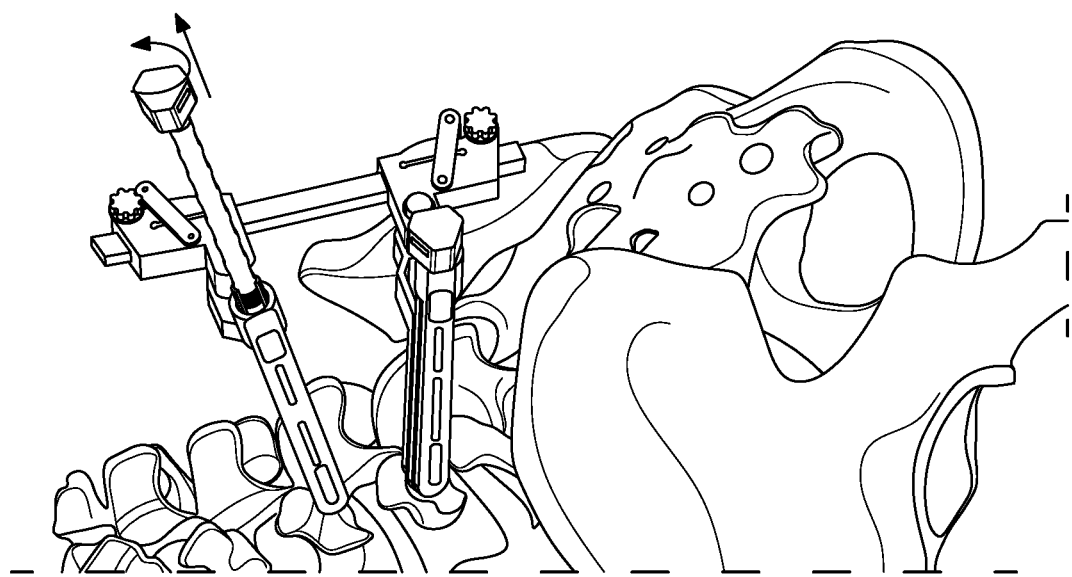
FIG. 40 is plan view of a component of the surgical instrument shown in FIG. 1 coupled to a component of the additional surgical instrument and a component of the second one of the surgical instruments shown in FIG. 1 coupled to the portion of the additional surgical instrument.

Once movement of receiver 54 of bone screw 1056 relative to shank 206 of bone screw 1056 and/or movement of receiver 54 of bone screw 56 relative to shank 206 of bone screw 56 is prevented by inserting head lockers 296 into sleeve 16 of driver 1012 and/or sleeve 16 of driver 12, head locker 296 and sleeve 16 of driver 1012 can be removed from tower 288, as shown in FIG. 40. Likewise, head locker 296 and sleeve 16 of driver 12 can be removed from tower 292, leaving only instrument 290 coupled to bone screws 56, 1056. A spinal rod can then be inserted between arms 50, 52 of bone screw 56 and between arms 50, 52 of bone screw 1056 to selectively position vertebra V2 relative to vertebra V1.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, spinal implant system 10 may include one or a plurality of spinal rods, plates, connectors and/or bone screws for use with a single vertebral level or a plurality of vertebral levels.

In some embodiments, one or more bone screws, as described herein, may be engaged with tissue in various orientations, such as, for example, series, parallel, offset, staggered and/or alternate vertebral levels. In some embodiments, the bone screws may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
   an outer sleeve extending along a longitudinal axis between opposite proximal and distal ends, the outer sleeve defining a passageway;
   a knob sleeve positioned in the passageway, the knob sleeve defining a bore and a sleeve cavity;

a latch positioned in the sleeve cavity;
a shaft positioned in the bore and comprising a proximal end extending through the proximal end of the outer sleeve and a distal end extending through the distal end of the outer sleeve, the distal end of the shaft comprising a drive; and
an inner sleeve having a proximal end positioned between the knob sleeve and the shaft and an opposite distal end comprising a threaded outer surface, the proximal end of the inner sleeve defining a notch,
wherein the knob sleeve is movable relative to the outer sleeve to move the instrument between a first orientation in which the latch is positioned in the notch and the inner sleeve is prevented from translating relative to the outer sleeve along the longitudinal axis and a second orientation in which the latch is spaced apart from the notch and the inner sleeve is translatable relative to the outer sleeve along the longitudinal axis, the instrument being biased to the first orientation.

2. The surgical instrument recited in claim 1, wherein the knob sleeve includes at least one spring configured to bias the instrument to the first orientation.

3. The surgical instrument recited in claim 2, wherein the at least one spring extends parallel to the longitudinal axis.

4. The surgical instrument recited in claim 1, wherein the inner sleeve is removable from the outer sleeve, the knob sleeve and the shaft when the instrument is in the second orientation.

5. The surgical instrument recited in claim 1, wherein the knob sleeve is configured to translate relative to the outer sleeve along the longitudinal axis to move the instrument from the first orientation to the second orientation.

6. The surgical instrument recited in claim 1, wherein the knob sleeve is configured to translate proximally relative to the outer sleeve along the longitudinal axis to move the instrument from the first orientation to the second orientation.

7. The surgical instrument recited in claim 1, wherein the drive is configured for disposal in a socket of a screw while the threaded outer surface mates with a threaded inner surface of the screw.

8. The surgical instrument recited in claim 1, further comprising a screw, the drive being configured for disposal in a socket of the screw while the threaded outer surface mates with a threaded inner surface of the screw.

9. The surgical instrument recited in claim 1, wherein the proximal end of the outer sleeve defines an aperture, the knob sleeve comprising a proximal portion positioned in the aperture and a distal portion positioned in the passageway, the sleeve cavity being disposed in the proximal portion, the instrument further comprising a knob coupled to the proximal portion, the knob comprising a knob cavity, a first end of the latch being positioned in the knob cavity and an opposite second end of the latch being positioned in the sleeve cavity.

10. The surgical instrument recited in claim 9, wherein the latch defines a hole extending into the first end of the latch, the instrument further comprising a spring having a first end directly engaging the knob and a second positioned in the hole.

11. The surgical instrument recited in claim 10, wherein the spring extends perpendicular to the longitudinal axis.

12. The surgical instrument recited in claim 1, wherein the proximal end of the outer sleeve defines an aperture, the knob sleeve comprising a proximal portion positioned in the aperture and a distal portion positioned in the passageway, the sleeve cavity being disposed in the proximal portion, the proximal portion comprising spaced apart grooves disposed radially about the proximal portion, the instrument further comprising a knob coupled to proximal portion, the knob comprising spaced apart tabs disposed radially about the knob, the tabs each being aligned with one of the grooves, the instrument comprising a spring positioned in each of the grooves such that the springs each engage one of the tabs, the springs being configured to bias the instrument to the first orientation.

13. The surgical instrument recited in claim 12, wherein the springs extend parallel to the longitudinal axis.

14. The surgical instrument recited in claim 12, wherein the springs each include a proximal end that directly engages a proximal wall of the knob sleeve and an opposite distal end that directly engages one of the tabs, the proximal wall and the tabs each extending perpendicular to the longitudinal axis.

15. The surgical instrument recited in claim 1, wherein the knob sleeve has an inner surface defining a hexagonal configuration and the inner sleeve comprises an outer surface having a hexagonal configuration that mates with the inner surface of the knob sleeve that defines the hexagonal configuration of the knob sleeve such that rotating the knob sleeve relative to the outer sleeve also rotates the inner sleeve relative to the outer sleeve.

16. The surgical instrument recited in claim 1, wherein the shaft is permanently fixed relative to the outer sleeve.

17. The surgical instrument recited in claim 1, wherein the proximal end of the outer sleeve defines an aperture, the knob sleeve comprising a proximal portion positioned in the aperture and a distal portion positioned in the passageway, the sleeve cavity being disposed in the proximal portion, the instrument further comprising a knob coupled to proximal portion, the instrument comprising a pin that extends through the knob and into the knob sleeve to couple the knob to the knob sleeve such that rotation of the knob relative to the outer sleeve also rotates the knob sleeve relative to the outer sleeve.

18. The surgical instrument recited in claim 1, wherein the knob sleeve has an inner surface defining a first configuration and the inner sleeve comprises an outer surface having a second configuration that mates with the inner surface of the knob sleeve that defines the first configuration of the knob sleeve such that rotating the knob sleeve relative to the outer sleeve also rotates the inner sleeve relative to the outer sleeve.

19. A surgical instrument comprising:
an outer sleeve extending along a longitudinal axis between opposite proximal and distal ends, the proximal end defining an aperture, the distal end defining a passageway;
a knob sleeve defining a bore and having a proximal portion positioned in the aperture and a distal portion positioned in the passageway, the proximal portion defining a first sleeve cavity and a second sleeve cavity;
a knob coupled to the proximal portion by spaced apart pins that each extend through the knob and into the knob sleeve such that rotation of the knob relative to the outer sleeve also rotates the knob sleeve relative to the outer sleeve, the knob defining a first knob cavity aligned with the first sleeve cavity and a second knob cavity aligned with the second sleeve cavity;
a first latch having a first end positioned in the first knob cavity and a second end positioned in the first sleeve cavity, the first latch having a spring positioned in a hole in the first end of the first latch;

a second latch having a first end positioned in the second knob cavity and a second end positioned in the second sleeve cavity, the second latch having a spring positioned in a hole in the first end of the second latch;

a shaft positioned in the bore and comprising a proximal end extending through the proximal end of the outer sleeve and a distal end extending through the distal end of the outer sleeve, the distal end of the shaft comprising a drive, the shaft being permanently fixed relative to the outer sleeve; and an inner sleeve having a proximal end positioned between the knob sleeve and the shaft and an opposite distal end comprising a threaded outer surface, the proximal end of the inner sleeve including a circumferential notch, wherein the knob is movable relative to the outer sleeve to move the instrument between a first orientation in which the latches are positioned in the notch and the inner sleeve is prevented from translating relative to the outer sleeve along the longitudinal axis and a second orientation in which the latches are spaced apart from the notch and the inner sleeve is translatable relative to the outer sleeve along the longitudinal axis, the instrument being biased to the first orientation.

20. A surgical instrument comprising:

an outer sleeve extending along a longitudinal axis between opposite proximal and distal ends, the proximal end defining an aperture, the distal end defining a passageway;

a knob sleeve defining a bore and having a proximal portion positioned in the aperture and a distal portion positioned in the passageway, the proximal portion defining a first sleeve cavity and a second sleeve cavity;

a knob coupled to the proximal portion by spaced apart pins that each extend through the knob and into the knob shaft such that rotation of the knob relative to the outer sleeve also rotates the knob sleeve relative to the outer sleeve, the knob defining a first knob cavity aligned with the first sleeve cavity and a second knob cavity aligned with the second sleeve cavity;

a first latch having a first end positioned in the first knob cavity and a second end positioned in the first sleeve cavity, the first latch having a spring positioned in a hole in the first end of the first latch, the second end of the first latch including a first ramp;

a second latch having a first end positioned in the second knob cavity and a second end positioned in the second sleeve cavity, the second latch having a spring positioned in a hole in the first end of the second latch, the second end of the second latch including a second ramp;

a shaft positioned in the bore and comprising a proximal end extending through the proximal end of the outer sleeve and a distal end extending through the distal end of the outer sleeve, the distal end of the shaft comprising a drive, the shaft being permanently fixed relative to the outer sleeve; and an inner sleeve having a proximal end positioned between the knob sleeve and the shaft and an opposite distal end comprising a threaded outer surface, the proximal end of the inner sleeve including a circumferential flange defining a circumferential ramp and a notch, wherein the knob is movable relative to the outer sleeve to move the instrument between a first orientation, a second orientation and a third orientation, the inner sleeve being distal to the bore when the instrument is in the first orientation, the latches being positioned in the notch when the instrument is in the second orientation such that the inner sleeve is prevented from translating relative to the outer sleeve along the longitudinal axis, the latches being spaced apart from the notch and a portion of the inner sleeve being positioned in the bore when the instrument is in the third orientation such that the inner sleeve is translatable relative to the outer sleeve along the longitudinal axis; the instrument being biased to the first orientation, and wherein the circumferential ramp slides along the ramps of the latches as the instrument moves from the first orientation to the second orientation.

* * * * *